US009943545B2

(12) United States Patent
Rezner

(10) Patent No.: US 9,943,545 B2
(45) Date of Patent: Apr. 17, 2018

(54) STEM CELL CULTURE MEDIA AND METHODS OF ENHANCING CELL SURVIVAL

(71) Applicant: FATE THERAPEUTICS, INC., San Diego, CA (US)

(72) Inventor: Betsy Denise Rezner, San Diego, CA (US)

(73) Assignee: Fate Therapeutics, Inc., San Diego, CA (US)

(*) Notice: Subject to any disclaimer, the term of this patent is extended or adjusted under 35 U.S.C. 154(b) by 0 days.

(21) Appl. No.: 14/209,131

(22) Filed: Mar. 13, 2014

(65) Prior Publication Data

US 2015/0044176 A1  Feb. 12, 2015

Related U.S. Application Data

(60) Provisional application No. 61/792,818, filed on Mar. 15, 2013.

(51) Int. Cl.
| A61N 1/02 | (2006.01) |
| C12N 5/00 | (2006.01) |
| A61K 35/14 | (2015.01) |
| A01N 1/02 | (2006.01) |
| C12N 5/078 | (2010.01) |
| C12N 5/0789 | (2010.01) |

(52) U.S. Cl.
CPC ............ *A61K 35/14* (2013.01); *A01N 1/0221* (2013.01); *C12N 5/0634* (2013.01); *C12N 5/0647* (2013.01); *C12N 2500/34* (2013.01); *C12N 2500/92* (2013.01); *C12N 2501/02* (2013.01); *C12N 2501/10* (2013.01); *C12N 2501/20* (2013.01); *C12N 2533/70* (2013.01)

(58) Field of Classification Search
CPC .............. C12N 5/0634; C12N 2500/34; C12N 2501/10; C12N 2501/20; C12N 2501/02; C12N 5/06; C12N 5/0018
USPC ................................................ 435/404–408
See application file for complete search history.

(56) References Cited

U.S. PATENT DOCUMENTS

| 4,683,202 | A | 7/1987 | Mullis |
| 5,460,964 | A | 10/1995 | McGlave et al. |
| 5,635,387 | A | 6/1997 | Fei et al. |
| 5,677,136 | A | 10/1997 | Simmons et al. |
| 5,716,827 | A | 2/1998 | Tsukamoto et al. |
| 5,750,397 | A | 5/1998 | Tsukamoto et al. |
| 5,854,033 | A | 12/1998 | Lizardi |
| 6,610,719 | B2 | 8/2003 | Paralkar et al. |
| 6,747,037 | B1 | 6/2004 | Old et al. |
| 7,131,958 | B2 | 11/2006 | Deverre |
| 7,147,626 | B2 | 12/2006 | Goodman et al. |
| 2005/0074435 | A1 | 4/2005 | Casper et al. |
| 2006/0247214 | A1 | 11/2006 | DeLong et al. |
| 2010/0047213 | A1 | 2/2010 | Zeitlin et al. |
| 2012/0276632 | A1* | 11/2012 | Strunk ................. C12N 5/0018 435/407 |
| 2015/0044177 | A1* | 2/2015 | Hariri et al. ................. 424/93.7 |

FOREIGN PATENT DOCUMENTS

| WO | 2000/038663 | A2 | 7/2000 |
| WO | 2001/012596 | A1 | 2/2001 |
| WO | 2006/047476 | A2 | 5/2006 |
| WO | 2007/071456 | A1 | 6/2007 |
| WO | 2007/112084 | A2 | 10/2007 |
| WO | 2008/070310 | A2 | 6/2008 |
| WO | 2008/073748 | A1 | 6/2008 |
| WO | 2010/054271 | A1 | 5/2010 |
| WO | 2010/108028 | A2 | 9/2010 |
| WO | 2010108028 | A2 | 9/2010 |
| WO | 2011/060381 | A1 | 5/2011 |
| WO | 2012/021845 | A2 | 2/2012 |
| WO | 2013/082241 | A2 | 6/2013 |
| WO | 2013/082243 | A1 | 6/2013 |
| WO | 2014150602 | A1 | 9/2014 |

OTHER PUBLICATIONS

Madihally et al., Maintenance of CD34 expression during proliferation of CD34+ cord blood cells on glycosaminoglycan surfaces. Stem Cells, vol. 17, No. 5 (Sep. 1999) pp. 295-305.*
Dupuis et al., Prostaglandin E2 stimulates the growth of human blood CD34 progenitors. Prostaglandins & Other Lipid Mediators, vol. 55, No. 2-3 (Feb. 1998) pp. 179-186.*
Mitra et al., Are all colloids same? How to select the right colloid? Indian Journal of Anaesthesia, vol. 53, No. 5 (Oct. 2009) pp. 592-607.*
Holyoake et al., CD34+ positive haemopoietic cells: Biology and clinical applications. Blood Reviews, vol. 8 No. 2 (Jun. 1994) pp. 113-124.*
Barnes et al., Methods for growth of cultured cells in serum-free medium. Analytical Biochemistry, vol. 102 (1980) pp. 255-270.*
Moore et al., Modified RPMI 1640 culture medium. In Vitro Cellular & Developmental Biology, vol. 29A (Apr. 1993) p. 268.*
Barany, "Genetic disease detection and DNA amplification using cloned thermostable ligase," Proc. Natl. Acad. Sci. USA, 88(1):189-193 (1991).
Dupuis et al., "Prostaglandin E2 stimulates the growth of human blood CD34+ progenitors," Prostaglandins & Other Lipid Mediators, 55:179-186 (1998).
Fehér et al., "Prostagladin E2 as stimulator of haemopoietic stem cell proliferation," Nature, 247:550-551 (1974).
Gidali et al., "The Effect of E Type Prostaglandins on the Proliferation of Haemopoietic Stem Cells In Vivo," Cell Tissue Kinet., 10:365-373 (1977).
Goessling et al., "Genetic interaction of PGE2 and Wnt signaling regulates developmental specification of stem cells and regeneration," Cell, 136:1136-1147 (2009).
Goessling et al., "Genetic interaction of PGE2 and Wnt signaling regulates developmental specification of stem cells and regeneration," Cell, vol. 136, Supplemental Data (2009).
Goichberg et al., "cAMP-induced PKCzeta activation increases functional CXCR4 expression on human CD34+ hematopoietic progenitors," Blood, 107(3):870-879 (2006).

(Continued)

*Primary Examiner* — Kara Johnson
(74) *Attorney, Agent, or Firm* — Jones Day

(57) ABSTRACT

The invention provides improved methods for preparing hematopoietic cells for transplantation and the resulting improved hematopoietic cell compositions. The invention further relates to improved culture media and methods of culturing, processing, modulating, and expanding blood cell products for hematopoietic transplantation.

55 Claims, 4 Drawing Sheets

(56) References Cited

OTHER PUBLICATIONS

Guatelli et al., "Isothermal, in vitro amplification of nucleic acids by a mutienzyme reaction modeled after retroviral replication," Proc. Natl. Acad. Sci USA, 87:1874-1878 (1990).

Hanson et al., "16, 16-Dimethyl Prostaglandin E2 Induces Radioprotection in Murine Intestinal and Hematopoietic Stem Cells," Radiation Research, 103:96-203 (1985).

Hoggatt et al., "Prostaglandin E2 enhances hematopoietic stem cell homing, survival, and proliferation," Blood, 113(22):5444-5455 (2009).

Kahn et al., "Overexpression of CXCR4 on human CD34+ progenitors increases their proliferation, migration, and NOD/SCID repopulation," Gene Therapy, Blood, 103(8):2942-2949 (2004).

Kwoh et al., "Transcription-based amplification system and detection of amplified human immunodeficiency virus type 1 with a bead-based sandwich hybridization format," Proc. Natl. Acad. Sci. USA, 86:1173-1177 (1989).

Lizardi et al., "Exponential amplication of recombinant-RNA hybrization probes," Bio/Technology, 6:1197-1202 (1988).

Lord et al., "Prostaglandin E2: making more of your marrow," Cell Cycle, 6(24):3054-3057 (2007).

Mazur, "The role of intracellular freezing in the death of cells cooled at supraoptimal rates," Cryobiology, 14(3):251-272 (1977).

North et al., "Prostaglandin E2 regulates vertebrate haematopoietic stem cell homeostasis," Nature, 447:1007-1011, (2007).

Rubinstein et al., "Processing and cryopreservation of placental/umbilical cord blood for unrelated bone marrow reconstitution," Proc. Natl. Acad. Sci. USA, 92:10119-10122 (1995).

Schena et al., "Quantitative monitoring of gene expression patterns with a complementary DNA microarray," Science, 270:467-470 (1995).

Sieburg et al, "Predicting clonal self-renewal and extinction of hematopoietic stem cells," Proc. Natl. Acad Sci USA, 108(11):4370-4375 (2011).

Weis et al., "Detection of rare mRNAs via quantitative RT-PCR," Trends Genet, 8(8):263-264 (1992).

Basford et al., "The cord blood separation league table: a comparison of the major clinical grade harvesting techniques for cord blood stem cells," Int. J. Stem Cells, 3(1):32-45 (2010).

Cloutier et al., "An alternative to dextran for the thawing of cord blood units," Transfusion, 56(7):1786-1791 (2016).

Hirata et al., "Use of cryoprotectant-depleted allogeneic peripheral blood stem cells for transplantation," Hematology, 16(4):221-224 (2011).

Mairhofer et al., "Evaluation of a xeno-free protocol for long-term cryopreservation of cord blood cells," Cell Transplantation, 22:1087-1099 (2013).

Rubinstein et al., "Processing and cryopreservation of placental/umbilical cord blood for unrelated bone marrow reconstitution," Proc. Natl. Acad. Sci. USA, 92:10119-101222 (1995).

Shu et al., "Hematopoietic SCT with cryopreserved grafts: adverse reactions after transplantation and cryoprotectant removal before infusion," Bone Marrow Transplantation, 49:469-476 (2014).

* cited by examiner

STEM CELL CULTURE MEDIA AND METHODS OF ENHANCING CELL SURVIVAL

CROSS-REFERENCE TO RELATED APPLICATION

This application claims the benefit under 35 U.S.C. § 119(e) of U.S. Provisional Application No. 61/792,818, filed Mar. 15, 2013, which is incorporated by reference in its entirety.

BACKGROUND

Technical Field

The invention relates generally to improved culture media for manipulating cell populations, particularly populations of cells comprising hematopoietic stem cells, compositions thereof, and methods of using such media and compositions.

Description of the Related Art

Stem cells have utility for many clinical and research applications. For example, stem cells and their differentiated progeny can be used in cellular assays, drug screening, and toxicity assays. Stem cells also show promise for cell-based therapies, such as in regenerative medicine for the treatment of damaged tissue. One aspect of regenerative medicine being pursued is the use of hematopoietic stem cell transplants to treat an expanding list of cancers and degenerative disorders. According to the National Marrow Donor Program® (NMDP), an estimated 45,000 to 50,000 hematopoietic cell transplants (bone marrow, peripheral blood stem cells (PBSC), or cord blood transplants) are performed annually worldwide to treat patients with life-threatening malignant and non-malignant diseases (Horowitz M M. *Uses and Growth of Hematopoietic Cell Transplantation*. In: Blume K G, Forman S J, Appelbaum F R, eds. *Thomas' Hematopoietic Cell Transplantation*. 3rd ed. Malden, Mass: Blackwell; 2004:9-15). Moreover, approximately 4,800 patients are transplanted annually using unrelated donors or cord blood units through the NMDP.

For all of these applications, reproducible stem cell culture methods are needed to provide adequate numbers of cells of suitable quality for the purpose for which they are to be used. However, the art currently lacks any cell culture media that can preserve the biological activities of cells that undergo cell processing activities, including such processes as cryopreservation, thawing, resuspension, expansion, culturing, and maintenance of cell populations result in some degree of cell death. Thus, the art is in need of efficient cell culture media for processing, maintaining, manipulating, and expanding populations of cells for research and therapeutic purposes.

BRIEF SUMMARY

The invention generally provides improved culture media for manipulating cell populations, compositions thereof, and methods of using such media and compositions.

In various embodiments, a culture medium is provided comprising: (a) about 1% to about 20% polysaccharide; and (b) a chemically defined cell culture medium.

In a particular embodiment, the polysaccharide is a dextran.

In one embodiment, the polysaccharide is a dextran selected from the group consisting of: dextran-1, dextran-10, dextran-20, dextran-30, and dextran-40.

In a certain embodiment, the polysaccharide is dextran-40.

In an additional embodiment, the polysaccharide is a hydroxyethyl starch (HES).

In a certain embodiment, the polysaccharide is a HES selected from the group consisting of: hetastarch, hexastarch, pentastarch, and tetrastarch.

In one embodiment, the polysaccharide is hetastarch.

In another embodiment, the medium comprises about 1% to about 5% polysaccharide.

In yet another embodiment, the medium comprises about 6% polysaccharide.

In one particular embodiment, the medium comprises about 7% polysaccharide.

In one certain embodiment, the medium comprises about 8% polysaccharide.

In one additional embodiment, the medium comprises about 9% polysaccharide.

In one further embodiment, the medium comprises about 10% polysaccharide.

In a particular embodiment, the medium comprises about 1% to about 5% HSA.

In a further embodiment, the medium comprises about 2% HSA.

In another embodiment, the medium comprises about 3% HSA.

In an additional embodiment, the medium comprises about 4% HSA.

In one embodiment, the medium comprises about 5% HSA.

In a further embodiment, wherein the chemically defined cell culture medium is selected from the group consisting of: STEMSPAN-ACF, STEMSPAN-H3000, STEMSPAN-SFEM. STEMLINE II, STEMPRO 34, STEMXVIVO, Iscove's modified Dulbecco's medium (IMDM), Dulbecco's modified Eagle medium (DMEM), Roswell Park Memorial Institute medium (RPMI) 1640 medium, McCoy's SA medium, minimum essential medium alpha medium (alpha-MEM), basal medium Eagle (BME), Fischer's medium, medium199, F-12K nutrient mixture medium (Kaighn's modification, F-12K), and X-vivo 20.

In a particular embodiment, the chemically defined cell culture medium is selected from the group consisting of: STEMSPAN-ACF, STEMSPAN-H3000, and STEMSPAN-SFEM.

In a certain embodiment, the chemically defined cell culture medium is STEMSPAN.

In another certain embodiment, the culture medium further comprises one or more growth factors or cytokines.

In one certain embodiment, the chemically defined culture medium comprises one or more growth factors or cytokines selected from the group consisting of: flt3-ligand (FLT3); thrombopoietin (TPO), stem cell factor (SCF), epidermal growth factor (EGF), transforming growth factor-beta (TGF-β), basic fibroblast growth factor (bFGF), interleukin-3 (IL3), interleukin-6 (IL6), and interleukin-9 (IL9).

In one embodiment, the culture medium further comprises an agent selected from the group consisting of a cAMP analogue or enhancer, a Gα-s activator, and a prostaglandin pathway agonist.

In a particular embodiment, the prostaglandin pathway agonist selectively binds the PGE2 EP2 or PGE2 EP4 receptor.

In an additional embodiment, the prostaglandin pathway agonist comprises PGE2, or a PGE2 analogue or derivative.

In a further embodiment, the prostaglandin pathway agonist is selected from the group consisting of: PGE2, 16,16- dmPGE2, 15(S)-15-methyl PGE2, 20-ethyl PGE2, and 8-iso-16-cyclohexyl-tetranor PGE2.

In a further particular embodiment, the prostaglandin pathway agonist comprises 16,16-dmPGE2.

In various embodiments, a composition is provided comprising: (a) a population of cells comprising hematopoietic cells; (b) about 1% to about 20% polysaccharide; and (c) a chemically defined cell culture medium.

In one embodiment, the population of cells is selected from the group consisting of: bone marrow cells (BMCs), umbilical cord blood cells (UCBCs), placental blood cells, mobilized peripheral blood cells (mPBCs), hematopoietic stem cells (HSCs), hematopoietic progenitor cells (HPCs), and CD34+ cells.

In a particular embodiment, the population of cells is selected from the group consisting of: bone marrow, umbilical cord blood, placental blood, or mobilized peripheral blood.

In another particular embodiment, the hematopoietic cells are selected from the group consisting of: hematopoietic stem cells (HSCs), hematopoietic progenitor cells (HPCs), and CD34+ cells.

In a certain embodiment, the hematopoietic cells comprise a purified population of CD34+ cells.

In an additional embodiment, the polysaccharide is a dextran.

In another embodiment, the polysaccharide is a dextran selected from the group consisting of: dextran-1, dextran-10, dextran-20, dextran-30, and dextran-40.

In one embodiment, the polysaccharide is dextran-40.

In a certain embodiment, the polysaccharide is a HES.

In a further embodiment, the polysaccharide is a HES selected from the group consisting of: hetastarch, hexastarch, pentastarch, and tetrastarch.

In a particular embodiment, the polysaccharide is hetastarch.

In an additional embodiment, the composition comprises about 1% to about 5% polysaccharide.

In another embodiment, the composition comprises about 6% polysaccharide.

In a further certain embodiment, the composition comprises about 7% polysaccharide.

In one embodiment, the composition comprises about 8% polysaccharide.

In a particular embodiment, the composition comprises about 9% polysaccharide.

In a certain particular embodiment, the composition comprises about 10% polysaccharide.

In an additional particular embodiment, the composition comprises about 1% to about 5% HSA.

In a further particular embodiment, the composition comprises about 2% HSA.

In another particular embodiment, the composition comprises about 3% HSA.

In one particular embodiment, the composition comprises about 4% HSA.

In one embodiment, the composition comprises about 5% HSA.

In an additional embodiment, the chemically defined cell culture medium is selected from the group consisting of: STEMSPAN ACF, STEMSPAN-H3000, STEMSPAN-SFEM. STEMLINE II, STEMPRO 34, STEMXVIVO, Iscove's modified Dulbecco's medium (IMDM), Dulbecco's modified Eagle medium (DMEM), Roswell Park Memorial Institute medium (RPMI) 1640 medium, McCoy's 5A medium, minimum essential medium alpha medium (alpha-MEM), basal medium Eagle (BME), Fischer's medium, medium199, F-12K nutrient mixture medium (Kaighn's modification, F-12K), and X-vivo 20.

In one embodiment, the chemically defined cell culture medium is selected from the group consisting of: STEMSPAN-ACF, STEMSPAN-H3000, STEMSPAN-SFEM.

In a certain embodiment, the chemically defined cell culture medium is STEMSPAN.

In yet another embodiment, the composition further comprises one or more growth factors or cytokines.

In a particular embodiment, the chemically defined culture medium comprises one or more growth factors or cytokines selected from the group consisting of: flt3-ligand (FLT3); thrombopoietin (TPO), stem cell factor (SCF), interleukin-3 (IL3), interleukin-6 (IL6), and interleukin-6 (IL9).

In a certain embodiment, the composition further comprises an agent selected from the group consisting of: a cAMP analogue or enhancer, a Gα-s activator, and a prostaglandin pathway agonist.

In a further embodiment, the prostaglandin pathway agonist selectively binds the PGE2 EP2 or PGE2 EP4 receptor.

In a particular embodiment, the prostaglandin pathway agonist comprises PGE2, or a PGE2 analogue or derivative.

In an additional embodiment, the prostaglandin pathway agonist is selected from the group consisting of: PGE2, 16,16-dmPGE2, 15(S)-15-methyl PGE2, 20-ethyl PGE2, and 8-iso-16-cyclohexyl-tetranor PGE2.

In one embodiment, the prostaglandin pathway agonist comprises 16,16-dmPGE2.

In various embodiments, a method is provided for stabilizing a hematopoietic cell population for transplantation comprising: (a) thawing a cryopreserved hematopoietic cell population; and (b) transferring the thawed hematopoietic cell population into any one of the culture media according to any of the foregoing embodiments; wherein the transferred hematopoietic cell population has reduced cell lysis and increased CD34+ cell viability compared to a thawed control hematopoietic cell population that has been transferred to a control solution.

In a particular embodiment, the hematopoietic cell population is thawed at a temperature of about 20° C. to about 37° C.

In another embodiment, the hematopoietic cell population is thawed at a temperature of about 25° C.

In a further embodiment, the hematopoietic cell population is thawed at a temperature of about 30° C.

In one embodiment, the hematopoietic cell population is thawed at a temperature of about 37° C.

In a particular embodiment, the hematopoietic cell population is selected from the group consisting of: bone marrow cells (BMCs), umbilical cord blood cells (UCBCs), placental blood cells, mobilized peripheral blood cells (mPBCs), hematopoietic stem cells (HSCs), hematopoietic progenitor cells (HPCs), and CD34+ cells.

In an additional embodiment, the hematopoietic cell population is selected from the group consisting of: bone marrow, umbilical cord blood, placental blood, or mobilized peripheral blood.

In a particular embodiment, the hematopoietic cell population is selected from the group consisting of: hematopoietic stem cells (HSCs), hematopoietic progenitor cells (HPCs), and CD34+ cells.

In a certain embodiment, the hematopoietic cell population is a purified population of CD34+ cells.

In another embodiment, the cell lysis of the hematopoietic cell population is decreased about 10% compared to the cell lysis of the control hematopoietic cell population.

In one embodiment, the cell lysis of the hematopoietic cell population is decreased about 20% compared to the cell lysis of the control hematopoietic cell population.

In another embodiment, the cell lysis of the hematopoietic cell population is decreased about 30% compared to the cell lysis of the control hematopoietic cell population.

In an additional embodiment, the cell lysis of the hematopoietic cell population is decreased about 40% compared to the cell lysis of the control hematopoietic cell population.

In a certain embodiment, the cell lysis of the hematopoietic cell population is decreased about 50% compared to the cell lysis of the control hematopoietic cell population.

In a further embodiment, the cell lysis of the hematopoietic cell population is decreased about two-fold compared to the cell lysis of the control hematopoietic cell population.

In a particular embodiment, the cell lysis of the hematopoietic cell population is decreased about three-fold compared to the cell lysis of the control hematopoietic cell population.

In a further embodiment, the cell lysis of the hematopoietic cell population is decreased about five-fold compared to the cell lysis of the control hematopoietic cell population.

In one embodiment, the CD34+ cell viability of the hematopoietic cell population is increased about 10% compared to the CD34+ cell viability of the control hematopoietic cell population.

In an additional embodiment, the CD34+ cell viability of the hematopoietic cell population is increased about 20% compared to the CD34+ cell viability of the control hematopoietic cell population.

In a particular embodiment, the CD34+ cell viability of the hematopoietic cell population is increased about 30% compared to the CD34+ cell viability of the control hematopoietic cell population.

In another particular embodiment, the CD34+ cell viability of the hematopoietic cell population is increased about 40% compared to the CD34+ cell viability of the control hematopoietic cell population.

In another embodiment, the CD34+ cell viability of the hematopoietic cell population is increased about 50% compared to the CD34+ cell viability of the control hematopoietic cell population.

In one embodiment, the CD34+ cell viability of the hematopoietic cell population is increased about two-fold compared to the CD34+ cell viability of the control hematopoietic cell population.

In one embodiment, the CD34+ cell viability of the hematopoietic cell population is increased about three-fold compared to the CD34+ cell viability of the control hematopoietic cell population.

In a particular embodiment, the CD34+ cell viability of the hematopoietic cell population is increased about five-fold compared to the CD34+ cell viability of the control hematopoietic cell population.

In a certain particular embodiment, the hematopoietic cell population is modulated ex vivo.

In an additional embodiment, the modulation comprises contacting the hematopoietic cell population with an agent selected from the group consisting of: a cAMP analogue or enhancer, a Gα-s activator, and a prostaglandin pathway agonist.

In a certain embodiment, the prostaglandin pathway agonist selectively binds the PGE2 EP2 or PGE2 EP4 receptor.

In an additional certain embodiment, the prostaglandin pathway agonist comprises PGE2, or a PGE2 analogue or derivative.

In a certain further embodiment, the prostaglandin pathway agonist is selected from the group consisting of: PGE2, 16,16-dmPGE2, 15(S)-15-methyl PGE2, 20-ethyl PGE2, and 8-iso-16-cyclohexyl-tetranor PGE2.

In one embodiment, the prostaglandin pathway agonist comprises 16,16-dmPGE2. In a further embodiment, the hematopoietic cell population is contacted with the at least one agent for a time of about one hour to about four hours.

In a particular embodiment, the hematopoietic cell population is contacted with the at least one agent for a time of about one hour.

In an additional embodiment, the hematopoietic cell population is contacted with the at least one agent for a time of about two hours.

In a certain embodiment, the hematopoietic cell population is contacted with the at least one agent at a temperature of about 25° C. to about 37° C.

In another embodiment, the hematopoietic cell population is contacted with the at least one agent at a temperature of about 30° C.

In one embodiment, the hematopoietic cell population is contacted with the at least one agent at a temperature of about 37° C.

In a particular embodiment, the hematopoietic cell population is contacted with 10 μM 16,16-dmPGE2, at about 37° C., for about two hours.

In an additional embodiment, engraftment of the hematopoietic cell population is increased in vivo, compared to a non-modulated hematopoietic cell population.

In another additional embodiment, reconstitution of the hematopoietic cell population is increased in vivo, compared to a non-modulated hematopoietic cell population.

In an additional embodiment, homing of the hematopoietic cell population is increased in vivo, compared to a non-modulated hematopoietic cell population.

In one embodiment, proliferation of the hematopoietic cell population is increased in vivo, compared to a non-modulated hematopoietic cell population.

In one embodiment, expression of at least two genes selected from the group consisting of: CREM, GEM, NR4A2, NR4A3, IL1A, COX2, HEY1, CXCL2, CXCL3, and ULBP2 is increased by about 20-fold in the hematopoietic cell population compared to expression of the at least two genes in the control hematopoietic cell population.

In one particular embodiment, expression of at least five genes selected from the group consisting of: CREM, GEM, NR4A2, NR4A3, IL1A, COX2, HEY1, CXCL2, CXCL3, and ULBP2 is increased by about 10-fold in the hematopoietic cell population compared to expression of the at least five genes in the control hematopoietic cell population.

In another particular embodiment, expression of at least five genes selected from the group consisting of: CREM, GEM, NR4A2, NR4A3, IL1A, COX2, HEY1, CXCL2, CXCL3, and ULBP2 is increased by about 3-fold in the hematopoietic cell population compared to expression of the at least five genes in the control hematopoietic cell population.

In a certain particular embodiment, expression of at least five genes selected from the group consisting of: CREM, GEM, NR4A2, NR4A3, IL1A, COX2, HEY1, CXCL2, CXCL3, and ULBP2 is increased by about 2-fold in the hematopoietic cell population compared to expression of the at least five genes in the control hematopoietic cell population.

In a further particular embodiment, expression of the genes CREM, GEM, NR4A2, NR4A3, IL1A, COX2, HAS1, CXCL2, CXCL3, and CXCR4 is each increased by about 3-fold in the hematopoietic cell population compared to expression of the genes in the control hematopoietic cell population.

In an additional particular embodiment, expression of the genes CREM, GEM, NR4A2, NR4A3, IL1A, COX2, HAS1, CXCL2, CXCL3, and CXCR4 is each increased by about 2-fold in the hematopoietic cell population compared to expression of the genes in the control hematopoietic cell population.

In one embodiment, the hematopoietic cell population is administered to a subject.

In another embodiment, the hematopoietic cell population is allogeneic to the subject.

In yet another embodiment, the hematopoietic cell population is autologous to the subject.

In one particular embodiment, the subject has a disease, disorder, or condition selected from the group consisting of: ischemia, a non malignant blood disorder, an immunodeficiency, severe combined immunodeficiency (SCID), lymphocytopenia, thrombocytopenia, neutropenia, anemia, Fanconi's anemia, severe aplastic anemia, a congenital hemoglobinopathy, sickle cell disease, β-thalassemaia, sickle-cell disease, Wiskott-Aldrich syndrome, a metabolic storage disease, Hurler's disease, Hunter's disease, mannosidosis, a cancer, a hematological malignancy, acute leukemia, chronic myeloid leukemia chronic lymphoid leukemia, Hodgkin's lymphoma, non-Hodgkin's lymphoma, multiple myeloma, myelodysplastic syndrome, a non-hematological cancer, breast cancer, ovarian cancer, brain cancer, prostate cancer, lung cancer, colon cancer, skin cancer, liver cancer, and pancreatic cancer.

In various embodiments, a method is provided for increasing viability of a hematopoietic cell population for transplantation comprising: (a) thawing a cryopreserved hematopoietic cell population; and (b) transferring the thawed hematopoietic cell population into any one of the culture media according to any one of the foregoing embodiments.

In one embodiment, the hematopoietic cell population is thawed at a temperature of about 20° C. to about 37° C.

In a particular embodiment, the hematopoietic cell population is thawed at a temperature of about 25° C.

In a further embodiment, the hematopoietic cell population is thawed at a temperature of about 30° C.

In a further embodiment, the hematopoietic cell population is thawed at a temperature of about 37° C.

In an additional embodiment, the hematopoietic cell population is selected from the group consisting of: bone marrow cells (BMCs), umbilical cord blood cells (UCBCs), placental blood cells, mobilized peripheral blood cells (mPBCs), hematopoietic stem cells (HSCs), hematopoietic progenitor cells (HPCs), and CD34+ cells.

In one embodiment, the hematopoietic cell population is selected from the group consisting of: bone marrow, umbilical cord blood, placental blood, or mobilized peripheral blood.

In a particular embodiment, the hematopoietic cell population is selected from the group consisting of: hematopoietic stem cells (HSCs), hematopoietic progenitor cells (HPCs), and CD34+ cells.

In a certain embodiment, the hematopoietic cell population is a purified population of CD34+ cells.

In another embodiment, the cell lysis of the hematopoietic cell population is decreased about 10% compared to the cell lysis of a thawed control hematopoietic cell population that has been transferred to a control solution.

In a further embodiment, the cell lysis of the hematopoietic cell population is decreased about 20% compared to the cell lysis of a thawed control hematopoietic cell population that has been transferred to a control solution.

In one embodiment, the cell lysis of the hematopoietic cell population is decreased about 30% compared to the cell lysis of a thawed control hematopoietic cell population that has been transferred to a control solution.

In an additional embodiment, the cell lysis of the hematopoietic cell population is decreased about 40% compared to the cell lysis of a thawed control hematopoietic cell population that has been transferred to a control solution.

In a particular embodiment, the cell lysis of the hematopoietic cell population is decreased about 50% compared to the cell lysis of a thawed control hematopoietic cell population that has been transferred to a control solution.

In a particular embodiment, the cell lysis of the hematopoietic cell population is decreased about two-fold compared to the cell lysis of a thawed control hematopoietic cell population that has been transferred to a control solution.

In one certain embodiment, the cell lysis of the hematopoietic cell population is decreased about three-fold compared to the cell lysis of a thawed control hematopoietic cell population that has been transferred to a control solution.

In a further embodiment, the cell lysis of the hematopoietic cell population is decreased about five-fold compared to the cell lysis of a thawed control hematopoietic cell population that has been transferred to a control solution.

In one embodiment, the CD34+ cell viability of the hematopoietic cell population is increased about 10% compared to the CD34+ cell viability of a thawed control hematopoietic cell population that has been transferred to a control solution.

In one embodiment, the CD34+ cell viability of the hematopoietic cell population is increased about 20% compared to the CD34+ cell viability of a thawed control hematopoietic cell population that has been transferred to a control solution.

In a particular embodiment, the CD34+ cell viability of the hematopoietic cell population is increased about 30% compared to the CD34+ cell viability of a thawed control hematopoietic cell population that has been transferred to a control solution.

In another embodiment, the CD34+ cell viability of the hematopoietic cell population is increased about 40% compared to the CD34+ cell viability of a thawed control hematopoietic cell population that has been transferred to a control solution.

In an additional embodiment, the CD34+ cell viability of the hematopoietic cell population is increased about 50% compared to the CD34+ cell viability of a thawed control hematopoietic cell population that has been transferred to a control solution.

In a further embodiment, the CD34+ cell viability of the hematopoietic cell population is increased about two-fold compared to the CD34+ cell viability of a thawed control hematopoietic cell population that has been transferred to a control solution.

In a further particular embodiment, the CD34+ cell viability of the hematopoietic cell population is increased about three-fold compared to the CD34+ cell viability of a thawed control hematopoietic cell population that has been transferred to a control solution.

In a particular embodiment, the CD34+ cell viability of the hematopoietic cell population is increased about five-fold compared to the CD34+ cell viability of a thawed control hematopoietic cell population that has been transferred to a control solution.

In various embodiments, a method is provided for increasing total nucleated cell (TNC) count of a cryopreserved blood cell product for transplantation comprising: (a) thawing a cryopreserved blood cell product; and (b) transferring the thawed blood cell product into any one of the culture media according to any one of the foregoing embodiments.

In a certain embodiment, n the blood cell product is thawed at a temperature of about 20° C. to about 37° C.

In another certain embodiment, the blood cell product is thawed at a temperature of about 25° C.

In one embodiment, the blood cell product is thawed at a temperature of about 30° C.

In a particular embodiment, the blood cell product is thawed at a temperature of about 37° C.

In an additional embodiment, the blood cell product is selected from the group consisting of: bone marrow cells (BMCs), umbilical cord blood cells (UCBCs), placental blood cells, mobilized peripheral blood cells (mPBCs), hematopoietic stem cells (HSCs), hematopoietic progenitor cells (HPCs), and CD34+ cells.

In one embodiment, the blood cell product is selected from the group consisting of bone marrow, umbilical cord blood, placental blood, or mobilized peripheral blood.

In one particular embodiment, the blood cell product is selected from the group consisting of: hematopoietic stem cells (HSCs), hematopoietic progenitor cells (HPCs), and CD34+ cells.

In another embodiment, the blood cell product is a purified population of CD34+ cells.

In a further embodiment, the TNC count of the blood cell product is increased about 10% compared to the TNC count of a thawed control blood cell product that has been transferred to a control solution.

In a particular embodiment, the TNC count of the blood cell product is increased about 20% compared to the TNC count of a thawed control blood cell product that has been transferred to a control solution.

In a further particular embodiment, the TNC count of the blood cell product is increased about 30% compared to the TNC count of a thawed control blood cell product that has been transferred to a control solution.

In one embodiment, the TNC count of the blood cell product is increased about 40% compared to the TNC count of a thawed control blood cell product that has been transferred to a control solution.

In a certain embodiment, the TNC count of the blood cell product is increased about 50% compared to the TNC count of a thawed control blood cell product that has been transferred to a control solution.

In a particular embodiment, the TNC count of the blood cell product is increased about two-fold compared to the TNC count of a thawed control blood cell product that has been transferred to a control solution.

In an additional embodiment, the TNC count of the blood cell product is increased about three-fold compared to the TNC count of a thawed control blood cell product that has been transferred to a control solution.

In an additional embodiment, the TNC count of the blood cell product is increased about five-fold compared to the TNC count of a thawed control blood cell product that has been transferred to a control solution.

In various embodiments, a method is provided for preparing cryopreserved blood cell products for transplantation comprising: (a) thawing a cryopreserved blood cell product; and (b) transferring the thawed blood cell product into any one of the culture media according to any one of the foregoing embodiments.

In another embodiment, the blood cell product is thawed at a temperature of about 20° C. to about 37° C.

In a further embodiment, the blood cell product is thawed at a temperature of about 25° C.

In a particular embodiment, the blood cell product is thawed at a temperature of about 30° C.

In one embodiment, the blood cell product is thawed at a temperature of about 37° C.

In one additional embodiment, the blood cell product is selected from the group consisting of: bone marrow cells (BMCs), umbilical cord blood cells (UCBCs), placental blood cells, mobilized peripheral blood cells (mPBCs), hematopoietic stem cells (HSCs), hematopoietic progenitor cells (HPCs), and CD34+ cells.

In a particular embodiment, the blood cell product is selected from the group consisting of: bone marrow, umbilical cord blood, placental blood, or mobilized peripheral blood.

In a certain embodiment, the blood cell product is selected from the group consisting of: hematopoietic stem cells (HSCs), hematopoietic progenitor cells (HPCs), and CD34+ cells.

In one embodiment, the blood cell product is a purified population of CD34+ cells.

In one further embodiment, the blood cell product is modulated ex vivo.

In one certain embodiment, the modulation comprises contacting the blood cell product with an agent selected from the group consisting of: a cAMP analogue or enhancer, a Gα-s activator, and a prostaglandin pathway agonist.

In one particular embodiment, the prostaglandin pathway agonist selectively binds the PGE2 EP2 or PGE2 EP4 receptor.

In one additional embodiment, the prostaglandin pathway agonist comprises PGE2, or a PGE2 analogue or derivative.

In a particular embodiment, the prostaglandin pathway agonist is selected from the group consisting of: PGE2, 16,16-dmPGE2, 15(S)-15-methyl PGE2, 20-ethyl PGE2, and 8-iso-16-cyclohexyl-tetranor PGE2.

In another particular embodiment, the prostaglandin pathway agonist comprises 16,16-dmPGE2.

In one particular embodiment, the blood cell product is contacted with the at least one agent for a time of about one hour to about four hours.

In a further particular embodiment, the blood cell product is contacted with the at least one agent for a time of about one hour.

In a certain particular embodiment, the blood cell product is contacted with the at least one agent for a time of about two hours.

In an additional particular embodiment, the blood cell product is contacted with the at least one agent at a temperature of about 25° C. to about 37° C.

In an additional embodiment, the blood cell product is contacted with the at least one agent at a temperature of about 30° C.

In a certain embodiment, the blood cell product is contacted with the at least one agent at a temperature of about 37° C.

In one embodiment, the blood cell product is contacted with 10 µM 16,16-dmPGE2, at about 37° C., for about two hours.

In another embodiment, engraftment of the blood cell product is increased in vivo, compared to a non-modulated blood cell product.

In yet another embodiment, reconstitution of the blood cell product is increased in vivo, compared to a non-modulated blood cell product.

In still yet another embodiment, homing of the blood cell product is increased in vivo, compared to a non-modulated blood cell product.

In a particular embodiment, proliferation of the blood cell product is increased in vivo, compared to a non-modulated blood cell product.

In an additional embodiment, expression of at least two genes selected from the group consisting of: CREM, GEM, NR4A2, NR4A3, IL1A, COX2, HEY1, CXCL2, CXCL3, and ULBP2 is increased by about 20-fold in the blood cell product compared to expression of the at least two genes in the control blood cell product.

In a further embodiment, expression of at least five genes selected from the group consisting of: CREM, GEM, NR4A2, NR4A3, IL1A, COX2, HEY1, CXCL2, CXCL3, and ULBP2 is increased by about 10-fold in the blood cell product compared to expression of the at least five genes in the control blood cell product.

In one embodiment, expression of at least five genes selected from the group consisting of: CREM, GEM, NR4A2, NR4A3, IL1A, COX2, HEY1, CXCL2, CXCL3, and ULBP2 is increased by about 3-fold in the blood cell product compared to expression of the at least five genes in the control blood cell product.

In a particular embodiment, expression of at least five genes selected from the group consisting of: CREM, GEM, NR4A2, NR4A3, IL1A, COX2, HEY1, CXCL2, CXCL3, and ULBP2 is increased by about 2-fold in the blood cell product compared to expression of the at least five genes in the control blood cell product.

In a certain embodiment, expression of the genes CREM, GEM, NR4A2, NR4A3, IL1A, COX2, HAS1, CXCL2, CXCL3, and CXCR4 is each increased by about 3-fold in the blood cell product compared to expression of the genes in the control blood cell product.

In another embodiment, expression of the genes CREM, GEM, NR4A2, NR4A3, IL1A, COX2, HAS1, CXCL2, CXCL3, and CXCR4 is each increased by about 2-fold in the blood cell product compared to expression of the genes in the control blood cell product.

In one embodiment, the blood cell product is administered to a subject.

In a further embodiment, the blood cell product is allogeneic to the subject.

In an additional embodiment, the blood cell product is autologous to the subject.

In a particular embodiment, the subject has a disease, disorder, or condition selected from the group consisting of: ischemia, a non malignant blood disorder, an immunodeficiency, severe combined immunodeficiency (SCID), lymphocytopenia, thrombocytopenia, neutropenia, anemia, Fanconi's anemia, severe aplastic anemia, a congenital hemoglobinopathy, sickle cell disease, β-thalassemaia, sickle-cell disease, Wiskott-Aldrich syndrome, a metabolic storage disease, Hurler's disease, Hunter's disease, mannosidosis, a cancer, a hematological malignancy, acute leukemia, chronic myeloid leukemia chronic lymphoid leukemia, Hodgkin's lymphoma, non-Hodgkin's lymphoma, multiple myeloma, myelodysplastic syndrome, a non-hematological cancer, breast cancer, ovarian cancer, brain cancer, prostate cancer, lung cancer, colon cancer, skin cancer, liver cancer, and pancreatic cancer.

In various embodiments, a culture medium is provided according to any one of the foregoing embodiments, wherein the culture medium maintains a TNC of at least 70% in a thawed whole cord blood sample modulated by contacting the sample with an agent that modulates a prostaglandin pathway for a duration of about 1 to about 24 hours, at a temperature of about 25° C. to about 37° C.

In a particular embodiment, the culture medium maintains the TNC of at least 75% in the thawed whole cord blood sample.

In one embodiment, the culture medium maintains the TNC of at least 80% in the thawed whole cord blood sample.

In a certain embodiment, the culture medium maintains the TNC of at least 85% in the thawed whole cord blood sample.

In a certain particular embodiment, the culture medium maintains the TNC of at least 90% in the thawed whole cord blood sample.

In a certain additional embodiment, the culture medium maintains the TNC of at least 95% in the thawed whole cord blood sample.

In another certain embodiment, the culture medium maintains the TNC of at least 99% in the thawed whole cord blood sample.

In a certain further embodiment, the agent is selected from the group consisting of: a cAMP analogue or enhancer, a Gα-s activator, and a prostaglandin pathway agonist.

In one particular embodiment, the agent selectively binds the PGE2 EP2 or PGE2 EP4 receptor.

In a particular embodiment, the agent comprises PGE2, or a PGE2 analogue or derivative.

In one embodiment, the agent is selected from the group consisting of: PGE2, 16,16-dmPGE2, 15(S)-15-methyl PGE2, 20-ethyl PGE2, and 8-iso-16-cyclohexyl-tetranor PGE2.

In a further embodiment, the agent comprises 16,16-dmPGE2.

In an additional embodiment, the whole cord blood sample is contacted with the at least one agent for a time of about one hour to about four hours.

In a certain embodiment, the whole cord blood sample is contacted with the at least one agent for a time of about one hour.

In another embodiment, the whole cord blood sample is contacted with the at least one agent for a time of about two hours.

In one embodiment, the whole cord blood sample is contacted with the at least one agent at a temperature of about 25° C. to about 37° C.

In one certain embodiment, the whole cord blood sample is contacted with the at least one agent at a temperature of about 30° C.

In one particular embodiment, the whole cord blood sample is contacted with the at least one agent at a temperature of about 37° C.

In another embodiment, the whole cord blood sample is contacted with 10 μM 16,16-dmPGE2, at about 37° C., for about two hours.

In a particular embodiment, the contacted whole cord blood sample expresses at least two genes selected from the group consisting of: CREM, GEM, NR4A2, NR4A3, IL1A, COX2, HEY1, CXCL2, CXCL3, and ULBP2 about 20-fold compared to expression of the at least two genes in a control blood cell product.

In one particular embodiment, the contacted whole cord blood sample expresses at least five genes selected from the group consisting of: CREM, GEM, NR4A2, NR4A3, IL1A, COX2, HEY1, CXCL2, CXCL3, and ULBP2 about 10-fold compared to expression of the at least five genes in a control blood cell product.

In another particular embodiment, the contacted whole cord blood sample expresses at least five genes selected from the group consisting of: CREM, GEM, NR4A2, NR4A3, IL1A, COX2, HEY1, CXCL2, CXCL3, and ULBP2 about 3-fold compared to expression of the at least five genes in a control blood cell product.

In an additional particular embodiment, the contacted whole cord blood sample expresses at least five genes selected from the group consisting of: CREM, GEM, NR4A2, NR4A3, IL1A, COX2, HEY1, CXCL2, CXCL3, and ULBP2 about 2-fold compared to expression of the at least five genes in a control blood cell product.

In a further particular embodiment, the contacted whole cord blood sample expresses the genes CREM, GEM, NR4A2, NR4A3, IL1A, COX2, HEY1, CXCL2, CXCL3, and ULBP2 about 10-fold compared to expression of the genes in a control blood cell product.

In a certain particular embodiment, the contacted whole cord blood sample expresses the genes CREM, GEM, NR4A2, NR4A3, IL1A, COX2, HEY1, CXCL2, CXCL3, and ULBP2 about 5-fold compared to expression of the genes in a control blood cell product.

In one embodiment, the contacted whole cord blood sample expresses the genes CREM, GEM, NR4A2, NR4A3, IL1A, COX2, HEY1, CXCL2, CXCL3, and ULBP2 about 3-fold compared to expression of the genes in a control blood cell product.

In a certain embodiment, the contacted whole cord blood sample expresses the genes CREM, GEM, NR4A2, NR4A3, IL1A, COX2, HEY1, CXCL2, CXCL3, and ULBP2 about 2-fold compared to expression of the genes in a control blood cell product.

In various embodiments, a whole cord blood sample thawed and transferred into a culture medium is provided according to any one of the foregoing embodiments, and modulated in the culture medium by contacting the sample with an agent that modulates a prostaglandin pathway for a duration of about 1 to about 24 hours, at a temperature of about 25° C. to about 37° C., comprising a TNC of at least 70%, wherein the sample is not subject to enrichment.

In a certain embodiment, the TNC is at least 75%.
In a particular embodiment, the TNC is at least 80%.
In one embodiment, the TNC is at least 85%.
In an additional embodiment, the TNC is at least 90%.
In another embodiment, the TNC is at least 95%.
In a particular embodiment, the TNC is at least 99%.

In a further embodiment, a thawed whole cord blood sample according to any one of the foregoing embodiments is provided, wherein the agent is selected from the group consisting of: a cAMP analogue or enhancer, a Gα-s activator, and a prostaglandin pathway agonist.

In one embodiment, a thawed whole cord blood sample according to any one of the foregoing embodiments is provided, wherein the agent selectively binds the PGE2 EP2 or PGE2 EP4 receptor.

In a particular embodiment, a thawed whole cord blood sample according to any one of the foregoing embodiments is provided, wherein the agent comprises PGE2, or a PGE2 analogue or derivative.

In a certain embodiment, a thawed whole cord blood sample according to any one of the foregoing embodiments is provided, wherein the agent is selected from the group consisting of: PGE2, 16,16-dmPGE2, 15(S)-15-methyl PGE2, 20-ethyl PGE2, and 8-iso-16-cyclohexyl-tetranor PGE2.

In another embodiment, a thawed whole cord blood sample according to any one of the foregoing embodiments is provided, wherein the agent comprises 16,16-dmPGE2.

In an additional embodiment, a thawed whole cord blood sample according to any one of the foregoing embodiments is provided, wherein the thawed whole cord blood sample is contacted with the at least one agent for a time of about one hour to about four hours.

In a further embodiment, a thawed whole cord blood sample according to any one of the foregoing embodiments is provided, wherein the thawed whole cord blood sample is contacted with the at least one agent for a time of about one hour.

In a particular embodiment, a thawed whole cord blood sample according to any one of the foregoing embodiments, wherein the thawed whole cord blood sample is contacted with the at least one agent for a time of about two hours.

In another particular embodiment, a thawed whole cord blood sample according to any one of the foregoing embodiments is provided, wherein the thawed whole cord blood sample is contacted with the at least one agent at a temperature of about 25° C. to about 37° C.

In one embodiment, a thawed whole cord blood sample according to any one of the foregoing embodiments is provided, wherein the thawed whole cord blood sample is contacted with the at least one agent at a temperature of about 30° C.

In another embodiment, a thawed whole cord blood sample according to any one of the foregoing embodiments is provided, wherein the thawed whole cord blood sample is contacted with the at least one agent at a temperature of about 37° C.

In one embodiment, a thawed whole cord blood sample according to any one of the foregoing embodiments is provided, wherein the thawed whole cord blood sample is contacted with 10 μM 16,16-dmPGE2, at about 37° C., for about two hours.

In an additional embodiment, a thawed whole cord blood sample according to any one of the foregoing embodiments is provided, wherein the thawed whole cord blood sample expresses at least two genes selected from the group consisting of: CREM, GEM, NR4A2, NR4A3, IL1A, COX2, HEY1, CXCL2, CXCL3, and ULBP2 about 20-fold compared to expression of the at least two genes in a control blood cell product.

In a certain embodiment, a thawed whole cord blood sample according to any one of the foregoing embodiments is provided, wherein the thawed whole cord blood sample expresses at least five genes selected from the group consisting of: CREM, GEM, NR4A2, NR4A3, IL1A, COX2, HEY1, CXCL2, CXCL3, and ULBP2 about 10-fold compared to expression of the at least five genes in a control blood cell product.

In an additional embodiment, a thawed whole cord blood sample according to any one of the foregoing embodiments is provided, wherein the thawed whole cord blood sample expresses at least five genes selected from the group consisting of: CREM, GEM, NR4A2, NR4A3, IL1A, COX2, HEY1, CXCL2, CXCL3, and ULBP2 about 3-fold compared to expression of the at least five genes in a control blood cell product.

In one embodiment, a thawed whole cord blood sample according to any one of the foregoing embodiments is provided, wherein the thawed whole cord blood sample expresses at least five genes selected from the group consisting of: CREM, GEM, NR4A2, NR4A3, IL1A, COX2, HEY1, CXCL2, CXCL3, and ULBP2 about 2-fold compared to expression of the at least five genes in a control blood cell product.

In a further embodiment, a thawed whole cord blood sample according to any one of the foregoing embodiments is provided, wherein the thawed whole cord blood sample expresses the genes CREM, GEM, NR4A2, NR4A3, IL1A, COX2, HEY1, CXCL2, CXCL3, and ULBP2 about 10-fold compared to expression of the genes in a control blood cell product.

In a certain embodiment, a thawed whole cord blood sample according to any one of the foregoing embodiments is provided, wherein the thawed whole cord blood sample expresses the genes CREM, GEM, NR4A2, NR4A3, IL1A, COX2, HEY1, CXCL2, CXCL3, and ULBP2 about 5-fold compared to expression of the genes in a control blood cell product.

In a particular embodiment, a thawed whole cord blood sample according to any one of the foregoing embodiments is provided, wherein the thawed whole cord blood sample expresses the genes CREM, GEM, NR4A2, NR4A3, IL1A, COX2, HEY1, CXCL2, CXCL3, and ULBP2 about 3-fold compared to expression of the genes in a control blood cell product.

In one embodiment, a thawed whole cord blood sample according to any one of the foregoing embodiments is provided, wherein the thawed whole cord blood sample expresses the genes CREM, GEM, NR4A2, NR4A3, IL1A, COX2, HEY1, CXCL2, CXCL3, and ULBP2 about 2-fold compared to expression of the genes in a control blood cell product.

DETAILED DESCRIPTION

A. Overview

Figure 1A:
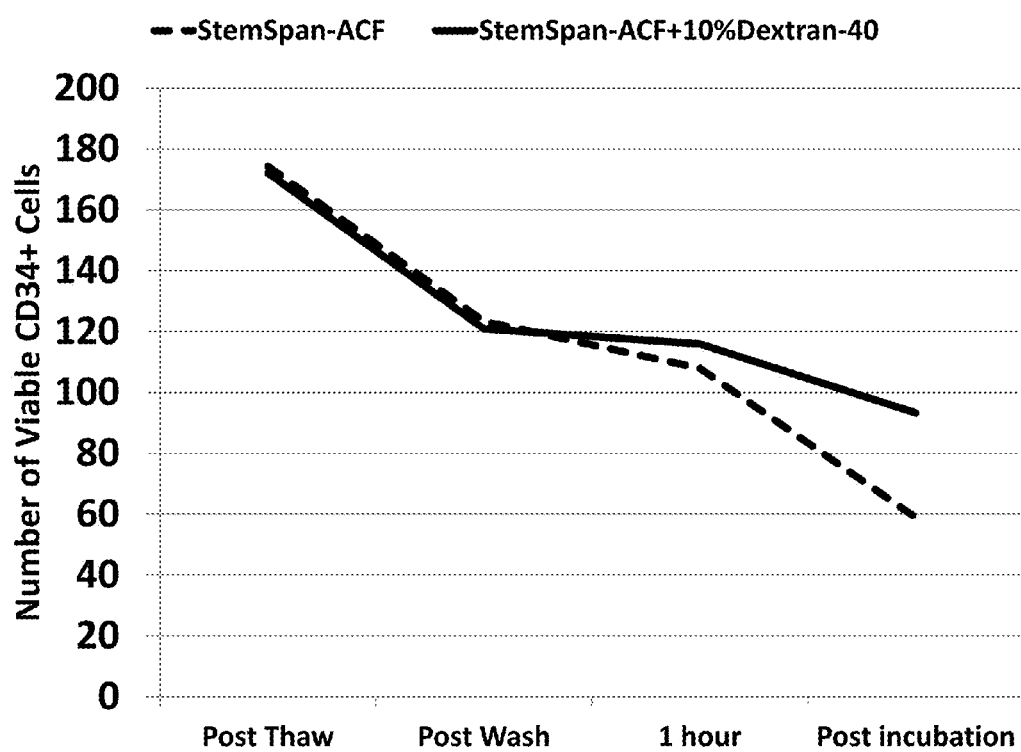
FIG. 1A shows the number of viable $CD34^+$ cells in the samples incubated in STEMSPAN-ACF with 8% Dextran-40 compared to STEMSPAN-ACF alone at post-thaw, post-wash, after one hour of incubation at 37° C. and after two hours of incubation at 37° C. (post-incubation).

The invention provides improved cell culture media for processing and modulating populations of cells, particularly compositions of hematopoietic stem cells. The invention also provides methods of preparing hematopoietic cell compositions for transplant therapy. Without wishing to be bound to any particular theory, it is contemplated that the culture media improves cell viability and reduces cell lysis of various cell types in the cell population (e.g., white blood cells, including granulocytes) during cell processing, including during preparation of the thawed cell populations, and during subsequent ex vivo manipulations of the cells. The cell culture media may decrease cell lysis by stabilizing the membranes of apoptosing cells.

In addition to a resulting increase in total nucleated cell count (TNC) during cell processing as a result of increasing cell stability and decreasing cell lysis, by preventing the release of intracellular components the cell culture media prevents cell debris aggregation in the blood cell product that may cause "clumping" within the cell product. Clumping in blood cell products may hinder further cell processing manipulation of the cell, and may also inhibit cellular processes, including modulation of the cells. Thus, by inhibiting apoptosis and lysis of cells (e.g., white blood cells, including granulocytes) during processing and modulation, culture media of the invention improves TNC recovery during processing, modulation, or expansion of the cell population. The culture media additionally enables modulation of cells, including activation of the cells by small molecules, as may be demonstrated by changes in gene and/or protein expression, where such modulation may be impaired or diminished in other cell culture or infusion media.

The culture media may be used in all cell processing steps including, cryopreserving, thawing, resuspension, modulating, expanding, or maintaining cell populations, particularly populations of cells comprising hematopoietic stem cells. The culture media may be particularly useful in processing and manipulating whole blood cell products, including whole umbilical cord blood, and mobilized peripheral blood, to prevent cell lysis of, for example, granulocytes and monocytes in the cell population and thereby reduce the occurrence of clumping in these blood products during processing.

The invention also provides compositions comprising hematopoietic stem cells with high biological activity that provide an improved source of hematopoietic cells for transplant therapy. The improved cell compositions have increased therapeutic properties that result in increased engraftment, increased hematopoietic reconstitution, increased homing to the bone marrow, and increased proliferation, in vivo. Accordingly, the improved methods and compositions contemplated herein may allow the use of a partial or single cord unit in cord blood transplantations.

In various embodiments, methods of preparing a population of cells comprising hematopoietic cells for transplant therapy are provided. The improved methods comprise the use of novel culture media that stabilizes hematopoietic cell populations allowing for modulation and enhancement of the hematopoietic cells; thereby increasing the likelihood of successful engraftment and hematopoietic reconstitution.

The practice of the invention will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Such techniques are explained fully in the literature. See, e.g., Sambrook, et al., *Molecular Cloning: A Laboratory Manual* (3rd Edition, 2001); Sambrook, et al.,

*Molecular Cloning: A Laboratory Manual* (2nd Edition, 1989); Maniatis et al., *Molecular Cloning: A Laboratory Manual* (1982); Ausubel et al., *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford, 1985); Anand, *Techniques for the Analysis of Complex Genomes*, (Academic Press, New York, 1992); *Transcription and Translation* (B. Hames & S. Higgins, Eds., 1984); Perbal, *A Practical Guide to Molecular Cloning* (1984); and Harlow and Lane, *Antibodies*, (Cold Spring Harbor Laboratory Press, Cold Spring Harbor, N.Y., 1998).

All publications, patents and patent applications cited herein are hereby incorporated by reference in their entirety.

B. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred embodiments of compositions, methods and materials are described herein. For the purposes of the present invention, the following terms are defined below.

The articles "a," "an," and "the" are used herein to refer to one or to more than one (i.e., to at least one) of the grammatical object of the article. By way of example, "an element" means one element or more than one element.

As used herein, the term "about" or "approximately" refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%.

It is understood that in some embodiments, the term "at least" can be substituted for the term "at least about."

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of:" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

In particular embodiments, the term "resuspension" or "dilution" refers to transferring the thawed cells into a culture medium as contemplated herein. The thawed cells can be transferred into the same volume of culture medium or into a larger volume. The thawed cells may be diluted 1, 2, 3, 4, 5, 6, 7, 8, 9, or 10 times or more into a culture medium as contemplated herein.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured or modulated in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The recitations "ex vivo administration," "ex vivo treatment," or "ex vivo modulation," relate generally to medical procedures in which one or more organs, cells, or tissues are obtained from a living or recently deceased subject, optionally purified/enriched, exposed to a treatment or procedure (e.g., an ex vivo administration step that involves incubating the cells with a composition or agent of the present invention to enhance expansion of particular cells, such as hematopoietic stem or progenitor cells). Cells treated ex vivo may be administered to the donor or to a different living subject. Such ex vivo therapeutic applications may also include an optional in vivo treatment or procedural step, such as by administering cells with therapeutic potential one or more times to the living subject. Both local and systemic administration is contemplated for these embodiments, according to well-known techniques in the art and as described elsewhere herein. The amount of therapeutic cells administered to a subject will depend on the characteristics of that subject, such as general health, age, sex, body weight, and tolerance to drugs, as well as the degree, severity, and type of reaction to the drug and/or cell transplant.

The term "in vivo" refers generally to activities that take place inside an organism, such as cell engraftment, reconstitution, cell homing, self-renewal of cells, and expansion of cells. In one embodiment, the term "in vivo expansion" refers to the ability of a cell population to increase in number in vivo. In particular embodiments, the in vivo expansion include self-renewal and/or proliferation of stem cells.

As used herein, the term "engraftment" refers to the process of a cell integrating into a location, such as a tissue or site of injury, and becoming a resident cell in the tissue or at such site. Cells may engraft in the bone marrow, for instance, or in another location such as a site of injured or ischemic tissue.

In particular embodiments, the term "engraftment" refers to the process of hematopoietic cells locating to the bone marrow and becoming resident cells there. In certain embodiments, engraftment is substantially independent of cell proliferation and independent of reconstitution. "Increased engraftment" occurs when more cells engraft in a sample relative to the number of cells that engraft in a another sample, such as a control sample. In some embodiments, increased engraftment occurs when more cells in a treated sample of cells engrafts compared to the number of cells in a non-treated or control sample.

"Engraftment potential" refers to the ability of hematopoietic cells to engraft, and may be assessed by, for example, gene expression that indicates the cell has the potential for increased engraftment.

As used herein, the term "reconstitution" refers to the ability of one or more engrafted hematopoietic cells to repopulate or regenerate the hematopoietic system of a subject by giving rise to more progenitors and more differentiated hematopoietic cell types. In particular embodiments, reconstitution refers to the process of engrafted hematopoietic stem and/or progenitor cells repopulating the hematopoietic system. Long-term reconstitution requires engraftment. "Increased hematopoietic reconstitution" occurs when more of the hematopoietic system is reconstituted with cells in a sample compared to cells in a different sample, such as a treated sample versus a non-treated sample, which may only partially or preferentially reconstitute certain hematopoietic lineages. "Reconstitution potential" refers to the ability of hematopoietic cells to reconstitute the hematopoietic system, and may be assessed by, for example, gene expression that indicates that the cell has the potential for increased reconstitution.

"Homing" refers to the ability of HSPCs to localize, i.e., travel, to a particular area or tissue. Homing may include localization of administered HSPCs to the bone marrow or to another location such as a site of injured or ischemic tissue. "Increased homing" occurs when more cells migrate to a target tissue in a sample compared to the number of cells that migrate to the target tissue in a different sample, such as the migration seen in a treated sample as compared to an untreated sample. "Homing potential" the ability of hematopoietic cells to migrate to a target tissue, and may be assessed by, for example, gene expression that indicates that the cell has the potential for increased homing.

As used herein, the term "proliferation" refers to an increase in cell division, either symmetric or asymmetric division of cells. In particular embodiments, "proliferation" refers to the symmetric or asymmetric division of stem and/or progenitor. "Increased proliferation" occurs when there is an increase in the number of cells in a treated sample compared to cells in a non-treated sample. "Proliferation potential" refers to gene expression characteristics of hematopoietic cells that indicate the cell has the potential for increased proliferation.

As used herein, the terms "treatment," "treating," and the like, refer to obtaining a desired pharmacologic and/or physiologic effect, including without limitation achieving an improvement or elimination of symptoms of a disease. The effect may be prophylactic in terms of completely or partially preventing a disease or symptom thereof and/or may be therapeutic in terms of achieving an improvement or elimination of symptoms, or providing a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; (c) relieving the disease, e.g., causing regression of the disease, e.g., to completely or partially eliminate symptoms of the disease; and (d) restoring the individual to a pre-disease state, e.g., reconstituting the hematopoietic system.

By "enhance" or "promote," or "increase" or "activate" refers generally to the ability of an agent to produce or cause a greater physiological response (i.e., downstream effects) in a cell, as compared to the response caused by either vehicle or a control molecule/composition, e.g., increased engraftment or reconstitution of hematopoietic stem and progenitor cells and increased in vivo stem cell expansion. A measurable physiological response may include an increase in hematopoietic stem and progenitor cell engraftment, reconstitution, viability, homing, self-renewal, and/or expansion, among others apparent from the understanding in the art and the description herein. In one embodiment, the measurable physiological response includes increased expression of a plurality of genes that are markers for therapeutic potential of hematopoietic cells, compared to the expression of the genes in a reference sample (e.g., control or untreated cells). An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response produced by vehicle (the absence of an agent) or a control composition.

By "decrease" or "lower," or "lessen," or "reduce," or "abate" refers generally to the ability of an agent to produce or cause a lesser physiological response (i.e., downstream effects) in a cell, as compared to the response caused by either vehicle or a control molecule/composition, e.g., decreased gene expression. In one embodiment, the decrease can be a decrease in gene expression or a decrease in cell signaling that normally is associated with a reduction of cell viability. An "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7, 1.8, etc.) the response produced by vehicle (the absence of an agent) or a control composition.

By "maintain," or "preserve," or "maintenance," or "no change," or "no substantial change," "no substantial increase," or "no substantial decrease" refers generally to the ability of a agent to produce or cause a comparable physiological response (i.e., downstream effects) in a cell, as compared to the response caused by either vehicle or a control molecule/composition (reference response). A comparable response is one that is not significantly different or measurably different from the reference response.

The "therapeutic potential" of a cell refers to the therapeutic quality of the cell, the cell's ability to provide a therapeutic benefit when administered to a subject. In particular embodiments, the therapeutic potential of a cell can be measured, quantified, determined, identified, or validated by increased expression of a plurality of genes and/or by the presence of a particular gene expression signature that indicates the cell's therapeutic potential. In one embodiment, therapeutic potential refers to a cell's ability to home and engraft to a particular tissue, organ, or site of injury. In a particular embodiment, therapeutic potential refers to a cell's ability to reconstitute the hematopoietic system of a subject. In a certain embodiment, therapeutic potential refers to a cell's ability undergo self-renewal in vivo once administered to a subject. In particular embodiments, the terms "therapeutic cell," "cell with therapeutic potential," and "cell having therapeutic potential" are used interchangeably.

In particular embodiments, cells that have increased expression of a plurality of genes and/or a particular gene expression signature have "sufficient therapeutic potential." The therapeutic potential of the cells is sufficient is they have the ability to engraft, the ability to reconstitute cell lineages, and/or the ability to proliferate when administered to a subject.

In certain embodiments, cells with therapeutic potential comprise unique or substantially unique gene and/or protein expression. The cells comprising unique or substantially unique expression are deemed to have therapeutic potential. In particular embodiments, the phrase "expression of a plurality of genes" refers to gene expression, the expression of mRNA. In other embodiments, the phrase "expression of a plurality of genes" refers to the level of protein expression.

A "plurality" of genes refers to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500 or more genes, including any intervening number of genes.

As used herein, the term "gene expression profile," "gene expression signature," "gene expression panel," "gene panel," or "gene signature" refers to the levels of expression of a plurality (i.e., more than one) of genes measured for the same sample, i.e., a population of cells. A gene expression signature may be defined so as to identify a group of genes "signature genes" or a "plurality of genes" that serves to distinguish the therapeutic cells or cells having therapeutic potential from existing cells in the art and/or control, vehicle, or non-treated cells.

A "signature gene", as used herein, means any gene in a group of signature genes or plurality of genes. For clarity, signature genes do not include housekeeping genes.

"Gene expression" as used herein refers to the relative levels of expression and/or pattern of expression of a gene in a biological sample, such as the stem and progenitor cells, or population of cells comprising stem or progenitor cells. In particular embodiments, the stem or progenitor cells are hematopoietic stem and progenitor cells.

"Genetic modification" refers to a temporary or permanent modification of a cell's genome, for example by insertion of a polynucleotide sequence in a viral or plasmid vector, or by homologous recombination or non-homologous end joining.

As used herein, the term "gene therapy" refers to the introduction of a polynucleotide into a cell that restores, corrects, or modifies the gene and/or expression of the gene. In particular embodiments, the gene therapy modifies the genome, and in other embodiments, the gene therapy is episomal.

As used herein, the phrases "detecting expression," "determining expression," and "measuring expression" refer to determining the quantity or presence of an RNA transcript or its expression product of a gene. Methods for detecting expression of genes, that is, gene expression profiling, include methods based on hybridization analysis of polynucleotides, methods based on sequencing of polynucleotides, immunohistochemistry methods, and proteomics-based methods. The methods generally detect expression products (e.g., mRNA) of the genes of interest. In some embodiments, PCR-based methods, such as reverse transcription PCR (RT-PCR) (Weis et al., TIG 8:263-64, 1992), and array-based methods such as microarray (Schena et al., Science 270:467-70, 1995) are used.

General methods for RNA extraction are well known in the art and are disclosed in standard textbooks of molecular biology, including Ausubel et al., ed., Current Protocols in Molecular Biology, John Wiley & Sons, New York 1987-1999. In particular, RNA isolation can be performed using a purification kit, a buffer set and protease from commercial manufacturers, such as Qiagen (Valencia, Calif.), according to the manufacturer's instructions. For example, total RNA from cells in culture can be isolated using Qiagen RNeasy mini-columns. Isolated RNA can be used in hybridization or amplification assays that include, but are not limited to, PCR analyses and probe arrays. One method for the detection of RNA levels involves contacting the isolated RNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 60, 100, 250, or 500 nucleotides in length and sufficient to specifically hybridize under stringent conditions to an intrinsic gene of the present invention, or any derivative DNA or RNA. Hybridization of an mRNA with the probe indicates that the intrinsic gene in question is being expressed.

An alternative method for determining the level of gene expression in a sample involves the process of nucleic acid amplification, for example, by RT-PCR (U.S. Pat. No. 4,683, 202), ligase chain reaction (Barany, Proc. Natl. Acad. Sci. USA 88:189-93, 1991), self sustained sequence replication (Guatelli et al., Proc. Natl. Acad. Sci. USA 87:1874-78, 1990), transcriptional amplification system (Kwoh et al., Proc. Natl. Acad. Sci. USA 86:1173-77, 1989), Q-Beta Replicase (Lizardi et al., Bio/Technology 6:1197, 1988), rolling circle replication (U.S. Pat. No. 5,854,033), or any other nucleic acid amplification method, followed by the detection of the amplified molecules using techniques well known to those of skill in the art.

Numerous different PCR or qPCR protocols are known in the art and exemplified herein below and can be directly applied or adapted for use using the cell potency assays contemplated herein to determine therapeutic potential. Quantitative PCR (qPCR) (also referred as real-time PCR) is preferred under some circumstances because it provides not only a quantitative measurement, but also reduced time and contamination. In some instances, the availability of full gene expression profiling techniques is limited due to requirements for fresh frozen tissue and specialized laboratory equipment, making the routine use of such technologies difficult in a clinical setting. As used herein, "quantitative PCR (or "real time qPCR") refers to the direct monitoring of the progress of PCR amplification as it is occurring without the need for repeated sampling of the reaction products. In quantitative PCR, the reaction products may be monitored via a signaling mechanism (e.g., fluorescence) as they are generated and are tracked after the signal rises above a background level but before the reaction reaches a plateau. The number of cycles required to achieve a detectable or "threshold" level of fluorescence varies directly with the concentration of amplifiable targets at the beginning of the PCR process, enabling a measure of signal intensity to provide a measure of the amount of target nucleic acid in a sample in real time.

C. Culture Media

In various embodiments, improved culture media for the manipulation of blood cell products are contemplated. The culture media increases total nuclear cell (TNC) count and cell viability of blood cell products during processing, including during cryopreservation, thawing, resuspension, culturing, or manipulation, including in blood cell products that have been thawed and/or modulated or expanded in vitro or ex vivo by one or more agents. The cell culture media also increases stability of the blood cell product by stabilizing the membranes of apoptosing cells, thereby decreasing cell lysis, preventing cell debris aggregation, and preventing the release of intracellular components that can inhibit cellular processes. In one embodiment, the cell culture media comprises a stock cell culture media used for culturing stem cells that is supplemented with a polysaccharide. In some embodiments, the cell culture media comprises a chemically defined stock basal media, such as any defined basal media suitable for supporting the maintenance, growth, and/or differentiation of stem cells, such as conventional human embryonic stem cell media, that is supplemented with a polysaccharide. In particular embodiments, a culture medium comprises polysaccharides, human serum albumin (HSA), and a chemically defined medium.

In some embodiments, the culture media are suitable for one or more of freezing, thawing, resuspension, processing or purification, modulation with one or more agents, or expansion of hematopoietic cells, e.g., HSPCs. In certain embodiments, the culture media are suitable for thawing, resuspension, processing or purification, modulation, expansion, and administration of hematopoietic cells to a subject. In further embodiments, the culture media are suitable for thawing, resuspension, processing or purification, modulation, and expansion of hematopoietic cells and the hematopoietic cells are subsequently washed with a pharmaceutically acceptable cell culture medium for administration to a subject.

1. Polysaccharides

In one embodiment, a cell culture medium or composition comprises one or more low molecular weight polysaccharides. A "polysaccharide" refers to any of a large class of long-chain sugars composed of monosaccharides. Because the chains may be unbranched or branched and the monosaccharides may be of one, two, or occasionally more kinds, polysaccharides can be categorized in various ways. In particular embodiments, cell culture media and compositions comprise about 1% to about 20% polysaccharide, about 1% to about 15% polysaccharide, about 1% to about 10% polysaccharide, or about 5% to about 10% polysaccharide. In certain embodiments, the culture media and compositions may comprise at least about 2%, at least about 3%, at least about 4%, at least about 5%, at least about 6%, at least about 7%, at least about 8%, at least about 9%, at least about 10%, at least about 11%, at least about 12%, at least about 13%, at least about 14% at least about 15%, at least about 16%, at least about 17%, at least about 18%, at least about 19%, or at least about 20% polysaccharide.

Without wishing to be bound to any particular theory, it is contemplated that increasing the polysaccharide content in cell culture medium stabilizes the membranes of the cells after being thawed and prevents cell lysis in apoptosing cells, thereby increasing the TNC count and hematopoietic stem and progenitor cell (HSPC) viability of the blood cell product. In certain preferred embodiments, a culture medium or composition comprises a polysaccharide selected from the group consisting of a dextran and a starch.

a. Dextrans

In various embodiments, a cell culture medium or composition comprises one or more low molecular weight dextrans. Dextrans are polysaccharides composed of an α-D-1,6-glucose-linked glucan with side-chains 1-3 linked to the backbone units of the dextran biopolymer. The degree of branching is approximately 5%. The branches are mostly 1-2 glucose units long. Dextran can be obtained from fermentation of sucrose-containing media by *Leuconostoc mesenteroides* B512F. Dextrans are isotonic and can be stored at room temperature.

Illustrative examples of low molecular weight dextrans include dextrans with a molecular weight of about 1000 Da (dextran-1), about 10,000 Da (dextran-10), about 20,000 Da (dextran-20), about 30,000 Da (dextran-30), about 40,000 Da (dextran-40), or about 50,000 Da (dextran-50).

In particular embodiments, a cell culture medium or composition comprises at least 1.0%, at least 2.0%, at least 3.0%, at least 4.0%, at least 5.0%, at least 6.0%, at least 7.0%, at least 8.0%, at least 9.0%, at least 10.0%, at least 11.0%, at least 12.0%, at least 13.0%, at least 14.0%, at least 15.0%, at least 16.0%, at least 17.0%, at least 18.0%, at least 19.0%, or at least 20.0% dextran. In certain embodiments, a cell culture medium or composition comprises about 1% to about 20% dextran, about 2.5% to about 15% dextran, about 5% to about 12.5% dextran, or about 5% to about 10% dextran. In one embodiment, the dextran is one or more of dextran-1, dextran-10, dextran-20, dextran-30, dextran-40, or dextran-50. In a particular embodiment, the dextran is dextran-40.

b. Hydroxyethyl Starch (HES)

In various embodiments, a cell culture medium or composition comprises one or more low molecular weight starches. A "starch" refers to polysaccharide that is a white odorless tasteless granular or powdery complex carbohydrate $(C_6H_{10}O_5)_x$ that is the chief storage form of carbohydrate in plants. In particular embodiments, a cell culture medium comprises a hydroxyethyl starch (HES).

HES is the parent name of a polymeric molecule made from a waxy species of either maize or sorghum and is composed primarily of amylopectin (98%). It is a highly branched polysaccharide closely resembling glycogen, formed by the reaction between ethylene oxide and amylopectin in the presence of an alkaline catalyst. The molecular weight and molar substitution can be adjusted by the degree of substitution of hydroxyl groups with hydroxyethyl groups at the $C_2$, $C_3$ and $C_6$ positions on the glucose molecule. The greater the substitution on position $C_2$ in relation to $C_6$ ($C_2$:$C_6$ ratio), the greater the half-life.

The number-averaged molecular weight (Mn) is the arithmetic mean of the molecular weights of the polymers in solution. Weight-averaged molecular weight (Mw) is the sum of the number of molecules at each number divided by the total of all molecules. This weight is generally larger when larger polymers are present in solution. The classification of different HES products includes the ratio of the Mw and the degree of substitution.

Illustrative examples of HES products include, but are not limited to hetastarch (0.7 degree substitution), hexastarch (0.6 degree substitution), pentastarch (0.5 degree substitution), and tetrastarch (0.4 degree substitution).

In particular embodiments, a cell culture medium or composition comprises about 1.0%, at least 2.0%, at least 3.0%, at least 4.0%, at least 5.0%, at least 6.0%, at least 7.0%, at least 8.0%, at least 9.0%, at least 10.0%, at least 11.0%, at least 12.0%, at least 13.0%, at least 14.0%, at least 15.0%, at least 16.0%, at least 17.0%, at least 18.0%, at least 19.0%, or at least 20.0% HES. In certain embodiments, the HES is selected from the group consisting of: hetastarch, hexastarch, pentastarch, and tetrastarch. In particular media formulations, a cell culture medium comprises one or more starches selected from the group consisting of: hetastarch, hexastarch, pentastarch, and tetrastarch. In one embodiment, a cell culture medium or composition comprises about 2.5% to about 12.5% HES, about 2.5% to about 10% HES, about 5% to about 12.5% HES, or about 5% to about 10% HES.

In one particular embodiment, a cell culture medium comprises both a dextran and a HES at a total starch concentration of 1.0%, at least 2.0%, at least 3.0%, at least 4.0%, at least 5.0%, at least 6.0%, at least 7.0%, at least 8.0%, at least 9.0%, at least 10.0%, at least 11.0%, at least 12.0%, at least 13.0%, at least 14.0%, at least 15.0%, at least 16.0%, at least 17.0%, at least 18.0%, at least 19.0%, or at least 20.0%.

2. Human Serum Albumin (HSA)

Human serum albumin (HSA) is the most abundant protein in human plasma with a molecular weight of 66,437 Da (based on amino acid composition). Commercial preparations contain varying degrees of post-translational modifications and genetic variants with molecular weight components mainly in the range of 66,437 to 66,600 Da.

In various embodiments, a cell culture medium or composition comprises HSA. In particular embodiments, a cell culture medium or composition comprises about 1.0%, about 1.25%, about 1.5%, about 1.75%, about 2.0%, about 2.25%, about 2.5%, about 2.75%, about 3.0%, about 3.25%, about 3.5%, about 3.75%, about 4.0%, about 4.25%, about 4.5%, about 4.75%, about 5.0%, about 5.25%, about 5.5%, about 5.75%, about 6.0%, about 6.25%, about 6.5%, about 6.75%, about 7.0%, about 7.25%, or about 7.5% HSA.

In another embodiment, a cell culture medium or composition comprises about 2.0% to about 7.5%, about 2.5% to about 6%, or about 4.0% to about 6%, or about 4% to about 5% HSA.

3. Chemically Defined Cell Culture Media

A "chemically defined medium" refers to a growth medium suitable for the in vitro or ex vivo cell culture of human or animal cells in which all of the chemical components are known. In a particular embodiment, a chemically defined medium is entirely free of animal-derived components and does not contain either fetal bovine serum, bovine serum albumin or human serum albumin as these products are derived from bovine or human sources and contain complex mixes of albumins and lipids. However, in certain embodiments, a composition may comprise a chemically defined media and one or more of the foregoing types of sera or additional agents, e.g., cytokines, growth factors, prostaglandin pathway agonists, and glucocorticoids.

A defined and humanized medium for the culture and proliferation and/or maintenance of human hematopoietic cells typically includes salts, vitamins, a source of glucose, minerals and amino acids. In particular embodiments, the defined medium may be supplemented with human serum or with a serum replacement. The serum replacement can be a commercially available product sold for that purpose or can be a formulated mixture of protein, such as serum albumin, vitamins, salts, minerals, a transferrin or transferrin substitute, and insulin or an insulin substitute. This serum replacement component may also be supplemented with selenium. In one embodiment, a culture medium comprises a defined medium that is supplemented with human serum albumin, vitamins, antioxidants, trace minerals, specific lipids, and cloned growth factors.

In particular embodiments, the defined medium is also a pharmaceutically acceptable cell-culture medium. Such compositions are suitable for administration to human subjects. Generally speaking, any medium that supports the maintenance, growth, and/or health of the hematopoietic cells of the invention are suitable for use as a pharmaceutical cell culture medium. In particular embodiments, the pharmaceutically acceptable cell culture medium is a serum free medium or chemically defined medium.

One illustrative example of a pharmaceutically acceptable cell culture medium includes Calcium Chloride Anhydrous CaCl3 (158.695 mg/L); Cupric Sulfate CuSO4 5H2O (0.000654 mg/L); Ferric Nitrate Fe(NO3) 9H2O (0.0751 mg/L); Ferric Sulfate FeSO47H2O (0.0209 mg/L); Potassium Chloride KCl (306.969 mg/L); Magnesium Chloride MgC12 (14.418 mg/L); Magnesium Sulfate MgSO4 (63.237 mg/L); Sodium Chloride NaCl (5021.73 mg/L); Sodium Bicarbonate NaHCO4 (1100 mg/L); Sodium Phosphate Monobasic NaH2PO4H2O (93.964 mg/L); Sodium Phosphate dibasic Na2HPO4 7H2O (35.753 mg/L); Zinc Sulfate ZnSO4 7H2O (0.217 mg/L); D-Glucose (Dextrose) (3836.3 mg/L); Phenol Red (8.127 mg/L); HEPES (3099.505 mg/L); Na Hypoxanthine (1.203 mg/L); Linoleic acid (0.0211 mg/L); DL-68-Thioctic Acid (0.0528 mg/L); Sodium Putrescine 2HCl (0.0407 mg/L); Putrescine 8 Sodium Selenite (2.5×10-6 mg/L); Sodium Pyruvate (40.1885 mg/L); Alanine (3.24 mg/L); Arginine HCl (116.255 mg/L); Asparagine (4.19 mg/L); Aspartic acid (3.347 mg/L); Cysteine H2O (9.445 mg/L); Cysteine 2HCl (15.752 mg/L); Glutamic acid (3.7 Glutamine (293.55 mg/L); Glycine (24.439 mg/L); Histidine HCl H2O (36.847 mg/L); Isoleucine (79.921 mg/L); Leucine (82.227 mg/L); Lysine HCl (118.937 mg/L); Methionine (23.679 mg/L); Phenylalanine (50.861 mg/L); Proline (12.564 mg/L); Serine (34.214 mg/L); Threonine (74.408 mg/L); Tryptophan (12.54 mg/L); Tyrosine 2Na+ 2 H2O (64.086 mg/L); Valine (73.606 mg/L); Biotin (0.00176 mg/L); D-Calcium panthenate (3.127 mg/L); Choline chloride (6.52 mg/L); Folic acid (3.334 mg/L); i-Inositol (9.904 mg/L); Niacinamide (3.079 mg/L); Pyridoxine HCl (3.022 mg/L); Riboflavine (0.31 mg/L); Thiamine HCl (3.092 mg/L); Thymidine (0.183 mg/L); and Vitamin B12 (0.512 mg/L).

Illustrative examples of chemically defined cell culture media suitable for use in the particular embodiments include, but are not limited to STEMSPAN ACF, STEMSPAN-H3000, STEMSPAN-SFEM, STEMLINE II, STEMPRO 34, STEMXVIVO, Iscove's modified Dulbecco's meditun (IMDM), Dulbecco's modified Eagle medium (DMEM), Roswell Park Memorial Institute medium (RPMI) 1640 medium, McCoy's 5A medium, minimum essential medium alpha medium (alpha-MEM), basal medium Eagle (BME), Fischer's medium, medium199, F-12K nutrient mixture medium (Kaighn's modification, F-12K), and X-vivo 20.

Illustrative examples of cytokines and/or hematopoietic cell growth factors include, but are not limited to flt3-ligand (FLT3), thrombopoietin (TPO), stem cell factor (SCF), epidermal growth factor (EGF), transforming growth factor-beta (TGF-β), basic fibroblast growth factor (bFGF), interleukin-3 (IL3), interleukin-6 (IL6), and interleukin-9 (IL9).

D. Compositions

In various embodiments, compositions comprising a blood cell product or partially isolated or purified hematopoietic cells and an improved culture media for the manipulation of blood cell products are contemplated. The cells of the composition have increased cell viability and can tolerate freeze/thaw processing, and in vitro or ex vivo modulation or expansion by one or more agents. The compositions also comprise apoptosing cells with increased stability, thereby decreasing cell lysis, preventing cell debris aggregation, and preventing the release of intracellular components that can inhibit subsequent cellular processes.

In particular embodiments, the compositions comprise a blood cell product or a population of isolated or purified hematopoietic cells. In some embodiments, the compositions are suitable for one or more of freezing, thawing, resuspension, processing or purification, modulation with one or more agents, or expansion. In certain embodiments, the compositions are suitable for thawing, resuspension, processing or purification, modulation, expansion, and administration to a subject. In further embodiments, the compositions are suitable for thawing, resuspension, processing or purification, modulation, and expansion, and are washed with a pharmaceutically acceptable cell culture medium for administration to a subject.

In particular embodiment, compositions comprise blood cell products or populations of hematopoietic cells that are HLA typed and may be matched or partially matched to a specific patient for transplantation.

At a minimum, HLA typing of the hematopoietic cell population is performed for six HLA loci, HLA-A, -B, and DR, for example, at low resolution/split antigen level.

In various embodiments, the blood cell product or population of hematopoietic cells comprises haplotyped hematopoietic stem or progenitor cells. In some embodiments, the population of cells comprising the therapeutic composition is HLA typed based on HLA-A, HLA-B, HLA-C, and HLA-DRB1. In particular embodiments, the population of cells is HLA typed based on the group consisting of HLA-DRB3/4/5, HLA-DQB1, and DPB1. In some embodiments, the population of cells comprising the therapeutic composition is matched with a specific human patient. In some embodiments, the population of HLA haplotyped cells has 4 out of 6 HLA matches with a specific human subject. HLA matching may be based on alleles or antigens, and combinations thereof. In some embodiments, the population of HLA haplotyped cells is a partial mismatch with a specific human subject, such as the subject to which the therapeutic composition is administered.

1. Blood Cell Products

In particular embodiments, compositions may comprise blood cell products or a portion thereof. Suitable blood cell products may be obtained from a blood bank or directly from a donor or patient. In particular embodiments, a composition comprises one or more units of a blood cell product. Suitable sources of blood cell products include, but are not limited to the bone marrow, the umbilical cord, umbilical cord blood, placental blood, the placenta, fetal blood, fetal liver, fetal spleen, Wharton's jelly, and mobilized peripheral blood.

In one embodiment, the blood cell product is umbilical cord blood. As used herein, the term "cord blood," "whole cord blood," "whole umbilical cord blood," or "umbilical cord blood" relates generally to the relatively small amount of blood (up to about 180 mL) from a newborn baby that returns to the neonatal circulation if the umbilical cord is not prematurely clamped. Cord blood is rich in HSPCs, and may be harvested and stored for later use according to techniques known in the art (see, e.g., U.S. Pat. Nos. 7,147,626 and 7,131,958, herein incorporated by reference for such methodologies). In one embodiment, whole cord blood does not include red blood cells and/or plasma.

In particular embodiments, a blood cell product requires a sufficient amount of hematopoietic cells for use in therapeutic applications. Increasing the amount of hematopoietic cells in a blood cell product may comprise a step of mobilizing hematopoietic stem and progenitor cells in a subject. A sufficient amount of hematopoietic stem and progenitor cells in the blood cell products contemplated for use in particular embodiments comprise at least about $1\times10^3$ HSPCs, at least about $1\times10^4$ HSPCs, at least about $1\times10^5$ HSPCs, at least about $1\times10^6$ HSPCs, at least about $1\times10^7$ HSPCs, at least about $1\times10^8$ HSPCs, at least about $1\times10^9$ HSPCs, at least about $1\times10^{10}$ HSPCs, at least about $1\times10^{11}$ HSPCs, at least about $1\times10^{12}$ HSPCs, at least about $1\times10^{13}$ HSPCs, at least about $1\times10^{14}$ HSPCs, or at least about $1\times10^{15}$ HSPCs.

"Hematopoietic stem cell mobilization" refers to the release of stem cells from the bone marrow or another tissue comprising hematopoietic stem and progenitor cells into the peripheral blood circulation for the purpose of leukapheresis, prior to stem cell transplantation. By increasing the number of stem cells harvested from the donor, the number of stem cells available for therapeutic applications can be significantly improved. Hematopoietic growth factors, e.g., granulocyte colony stimulating factor (G-CSF) or chemotherapeutic agents often are used to stimulate the mobilization. Commercial stem cell mobilization drugs exist and can be used in combination with G-CSF to mobilize sufficient quantities of hematopoietic stem and progenitor cells for transplantation into a subject. For example, G-CSF and Mozobil™ (Genzyme Corporation) can be administered to a donor in order to harvest a sufficient number of hematopoietic cells for transplantation. Other methods of mobilizing hematopoietic stem and progenitor cells would be apparent to one having skill in the art.

2. Hematopoietic Cells

In various embodiments, compositions contemplated herein comprise a purified or isolated population of cells comprising hematopoietic cells. As used herein, the term "isolated" refers to material that is removed from its original environment. For example, an "isolated population of cells," an "isolated source of cells," or "isolated HSPCs" and the like, as used herein, refer to in vitro or ex vivo separation of one or more cells from their natural cellular environment, and from association with other components of the tissue or organ, i.e., it is not significantly associated with in vivo substances. In particular embodiments, a composition comprises a population of hematopoietic stem or progenitor cells.

In particular embodiments, compositions comprise cells that are autologous/autogeneic ("self") or non-autologous ("non-self," e.g., allogeneic, syngeneic or xenogeneic) cells. "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells of the invention are allogeneic.

In various embodiments, the use of stem cells is preferred because they have the ability to differentiate into the appropriate cell types when administered to a particular biological niche, in vivo. The term "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3) of in vivo functional regeneration of tissues. As used herein, the term "progenitor" or "progenitor cells" refers to cells that have the capacity to self-renew and to differentiate into more mature cells. Progenitor cells have a reduced potency compared to pluripotent and multipotent stem cells.

As used herein, the term "hematopoietic stem and progenitor cell" or "HSPC" refers to a cell identified by the presence of the antigenic marker CD34 (CD34$^+$) and are therefore characterized as CD34$^+$ cells, and populations of such cells. In particular embodiments, the term "HSPC" refers to a cell identified by the presence of the antigenic marker CD34 (CD34$^+$) and the absence of lineage (Lin) markers and are therefore characterized as CD34$^+$/Lin(−) cells, and populations of such cells. It is recognized that the population of cells comprising CD34$^+$ and/or Lin(−) cells also includes hematopoietic progenitor cells. In one embodiment, a composition comprises a population of isolated CD34$^+$ cells.

Hematopoietic stem cells are multipotent stem cells that give rise to all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al., U.S. Pat. No. 5,635,387; McGlave, et al., U.S. Pat. No. 5,460,964; Simmons, P., et al, U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827). Hematopoietic progenitor cells (HSCs) give rise to committed hematopoietic progenitor cells (HPCs) that are capable of generating the entire repertoire of mature blood cells over the lifetime of an organism.

As used herein, the term "granulocytes" refers to a category of white blood cells characterized by the presence of granules in their cytoplasm. Granulocytes are often called polymorphonuclear leukocytes (PMN or PML) because of the varying shapes of the nucleus, which is usually lobed into three segments. Although the most abundant type of granulocytes are neutrophil granulocytes, the term "granulocyte" includes neutrophil granulocytes, eosinophil granulocytes, and basophil granulocytes.

In particular embodiments, HPSCs can be provided as a highly purified HSPC population (a homogenous population), or as a composition that comprises from 0.01% to about 100% of HSPCs (a heterogeneous population). Populations of cells comprising hematopoietic stem and progenitor cells include bone marrow cells, umbilical cord blood cells, placental blood cells, mobilized peripheral blood cells, hematopoietic stem cells, or hematopoietic progenitor cells. In particular embodiments, the number of HSPCs in a population of hematopoietic cells can be increased by mobilizing the stem and progenitor cells in the donor, as discussed supra.

In one embodiment, a composition comprises the amount of HSPCs in a partial or single cord of blood, or is at least $0.1 \times 10^5$ cells/kg of bodyweight, at least $0.5 \times 10^5$ cells/kg of bodyweight, at least $1 \times 10^5$ cells/kg of bodyweight, at least $5 \times 10^5$ cells/kg of bodyweight, at least $10 \times 10^5$ cells/kg of bodyweight, at least $0.5 \times 10^6$ cells/kg of bodyweight, at least $0.75 \times 10^6$ cells/kg of bodyweight, at least $1 \times 10^6$ cells/kg of bodyweight, at least $1.25 \times 10^6$ cells/kg of bodyweight, at least $1.5 \times 10^6$ cells/kg of bodyweight, at least $1.75 \times 10^6$ cells/kg of bodyweight, at least $2 \times 10^6$ cells/kg of bodyweight, at least $2.5 \times 10^6$ cells/kg of bodyweight, at least $3 \times 10^6$ cells/kg of bodyweight, at least $4 \times 10^6$ cells/kg of bodyweight, at least $5 \times 10^6$ cells/kg of bodyweight, at least $10 \times 10^6$ cells/kg of bodyweight, at least $15 \times 10^6$ cells/kg of bodyweight, at least $20 \times 10^6$ cells/kg of bodyweight, at least $25 \times 10^6$ cells/kg of bodyweight, or at least $30 \times 10^6$ cells/kg of bodyweight.

In particular embodiments, a composition comprises about $1 \times 10^3$ HSPCs, at least about $1 \times 10^4$ HSPCs, at least about $1 \times 10^5$ HSPCs, at least about $1 \times 10^6$ HSPCs, at least about $1 \times 10^7$ HSPCs, at least about $1 \times 10^8$ HSPCs, at least about $1 \times 10^9$ HSPCs, at least about $1 \times 10^{10}$ HSPCs, at least about $1 \times 10^{11}$ HSPCs, at least about $1 \times 10^{12}$ HSPCs, at least about $1 \times 10^{13}$ HSPCs, at least about $1 \times 10^{14}$ HSPCs, or at least about $1 \times 10^{15}$ HSPCs. In one embodiment, the HSPCs are CD34$^+$.

In particular embodiments, a composition comprises a population of cells that is about 95% to about 100% HSPCs. In some embodiments, the population of cells comprises less than about 0.1%, 0.5%, 1%, 2%, 5%, 10%, 15%, 20%, 25%, or 30% HSPCs. The population of cells in some embodiments comprises less than about 0.1%, 0.5%, 1%, 2%, 5%, 10%, 15%, 20%, 25%, or 30% HSPCs. In other embodiments, the population of cells is about 0.1% to about 1%, about 1% to about 3%, about 3% to about 5%, about 10%-about 15%, about 15%-20%, about 20%-25%, about 25%-30%, about 30%-35%, about 35%-40%, about 40%-45%, about 45%-50%, about 60%-70%, about 70%-80%, about 80%-90%, about 90%-95%, or about 95% to about 100% HSPCs.

In particular embodiments, the population of cells is about 0.1% to about 1%, about 1% to about 3%, about 3% to about 5%, about 10%-about 15%, about 15%-20%, about 20%-25%, about 25%-30%, about 30%-35%, about 35%-40%, about 40%-45%, about 45%-50%, about 60%-70%, about 70%-80%, about 80%-90%, about 90%-95%, or about 95% to about 100% HSPCs.

In various embodiments, the cells are not genetically modified cells. In other embodiments, the cells are genetically modified, such as by introducting of a polynucleotide, such as, for example a retroviral or lentiviral vector comprising a protein coding gene sequence. In some embodiments, the cell is genetically modified to correct a genetic defect and in other embodiments, the cell is genetically modified to increase or decrease production of a wild-type or mutant protein. Polynucleotides used to increase expression of a protein in a cell may comprise polynucleotide sequences to direct appropriate expression in the cell and a polynucleotide encoding the polypeptide sequence. Polynucleotides used to decrease expression of a protein in a cell may comprise polynucleotide sequences that target polynucleotides encoding the wild type polypeptide sequence for degradation.

3. Enhanced Hematopoietic Cells

In particular embodiments, compositions comprise human hematopoietic stem and progenitor cells wherein the stem cells have been contacted ex vivo with one or more agents capable of increasing the therapeutic properties of the cell. In one embodiment, human hematopoietic stem and progenitor cells have been contacted ex vivo with one or more agents that increase CXCR4 gene expression in the cells. In one preferred embodiment, the gene expression of CXCR4 is increased in the treated human hematopoietic stem cells at least about 2, 3, 4, 5, 10, 15, 20, or 30 fold compared to non-contacted hematopoietic stem and progenitor cells or cells treated with a vehicle control. "Enhanced hematopoietic stem and progenitor cell" or "enhanced HSPC" refers to a HSPC treated ex vivo with one or more agents that increase CXCR4 gene expression in the cell at least about 2, 3, 4, 5, 10, 15, 20, or 30 compared to control, vehicle or untreated cells.

As used herein, a "non-contacted," "untreated," or "control" cell is a cell that has not been treated, e.g., cultured, contacted, or incubated with an agent other than a control agent. Blood cell products or hematopoietic cells contacted with DMSO (a control agent), or contacted with another vehicle (10% dextran, 5% HSA, and 0.9% saline) are control cells.

The HSPCs of the invention are identified and are characterized by, a gene expression profile indicating high levels of CXCR4 expression. The HSPCs can also be characterized based upon increased CXCR4 gene expression and increased cell surface expression of CXCR4 polypeptide. In certain embodiments, the CXCR4 gene expression in the HSPCs of the invention is increased by at least 2, 3, 4, 5, 10, 15, 20, or 30 fold compared to the expression of CXCR4 in non-contacted cells. In certain embodiments, the CXCR4 gene expression in the HSPCs of the invention is increased by at least 30, 35, 40, 45, 50, 55, 60, 65, 70, 75, 80, 85, 90, 95, or 100 fold compared to the expression of CXCR4 in non-contacted cells.

In particular embodiments, CXCR4 gene expression in the HSPCs is increased by about 30 to about 80 fold compared to untreated HSPCs. In further embodiments, CXCR4 gene expression in the HSPCs is increased by about 40 to about 80 fold, about 50 to about 80 fold, about 60 to about 80 fold, or about 50 to about 70 fold, compared to untreated HSPCs.

CXCR4 gene expression or the gene expression signature of the treated HSPCs or an aliquot thereof may be determined after the cells are treated with one or more agents. For example, HSPCs may be treated ex vivo with one or more agents, washed to remove the agent(s), and the gene expression analyzed from a portion of the cells without further incubation of the cells.

An illustrative group of genes, e.g., "signature genes" for use in particular embodiments includes, but is not limited to: hairy/enhancer-of-split related with YRPW motif 1 (HEY1), UL16 binding protein 2 (ULBP2), hyaluronan synthase 1 (HAS1), GTP-binding protein GEM (GEM), renin (REN), collagen, type I, alpha 1 (COL1A1), cyclooxygenase 2 (COX-2), angiopoietin 1 (ANGPT1), chemokine (C—X—C motif) ligand 6 (CXCL6), prominin 1 (PROM1), bone morphogenetic protein 4 (BMP4), angiopoietin 2 (ANGPT2), inhibitor of kappaB kinase beta (IKBKB), platelet/endothelial cell adhesion molecule 1 (PECAM1), tyrosine kinase with immunoglobulin-like and EGF-like domains 1 (TIE1), amphiregulin (AREG), caspase 3 (CASP3), jagged 1 (JAG1), aryl hydrocarbon receptor nuclear translocator (ARNT), cAMP-responsive element modulator (CREM), connective tissue growth factor (CTGF), CD40 ligand (CD40L), BCL2-associated X protein (BAX), hepatocyte growth factor (HGF), superoxide dismutase 2 (SOD2), platelet derived growth factor B (PDGFB), thrombospondin 1 (THBS1), dual specificity protein phosphatase 4 (DUSP4), cysteine-rich protein 61 (CYR61), chemokine (C—X—C motif) ligand 1 (CXCL1), endothelial tyrosine kinase (TEK), CASP8 and FADD-like apoptosis regulator (CFLAR), insulin growth factor 2 (IGF2), chemokine (C—X—C motif) receptor 4 (CXCR4), matrix metalloprotease 2 (MMP2), fibroblast growth factor 2 (FGF2), prostaglandin-endoperoxide synthase 2 (PTGS2), RAS-related C3 botulinum substrate 2 (RAC2), platelet derived growth factor receptor (PDGFR), nuclear receptor subfamily 4, group A, member 2 (NR4A2), nuclear receptor subfamily 4, group A, member 3 (NR4A3), telomerase reverse transcriptase (TERT), transforming growth factor beta 1 (TGFB1), matrix metalloprotease 9 (MMP9), CD40 antigen (CD40), CD44 antigen (CD44), high mobility group box 1 (HMGB1), nitrogen oxide synthase 3 (NOS3), kinase insert domain receptor (KDR), integrin beta 1 (ITGB1), catenin (cadherin-associated protein), beta 1 (CTNNB1), colony stimulating factor 3 (CSF3), interleukin 8 (IL8), plasminogen activator, urokinase receptor (PLAUR), B-cell CLL/lymphoma 2 (BCL2), bone morphogenetic protein 2 (BMP2), colony stimulating factor 1 (CSF1), v-akt murine thymoma viral oncogene homolog 1 (AKT1), vascular endothelial growth factor A (VEGFA), intercellular adhesion molecule 1 (ICAM1), chemokine (C—X—C motif) ligand 3 (CXCL3), caspase 8 (CASP8), CD34 antigen (CD34), interleukin 1A (IL1A), CD47 antigen (CD47), chemokine (C—C motif) ligand 7 (CCL7), hypoxia inducible factor 1A (HIF1A), EDN1 (endothelin 1), sphingosine-1-phosphate receptor 1 (S1PR1), chemokine (C—C motif) receptor 1 (CCR1), SMAD family member 4 (SMAD4), fms-related tyrosine kinase 1 (FLT1), CD151 antigen (CD151), placental growth factor (PGF), nuclear factor of kappa light polypeptide gene enhancer in B-cells 1 (NFKB1), SMAD family member 2 (SMAD2), CXC chemokine receptor 7 (CXCR7), transforming growth factor beta 3 (TGFB3), chemokine (C—X—C motif) ligand 5 (CXCL5), cyclin D1 (CCND1), heparin-binding EGF-like growth factor (HBEGF), nuclear receptor subfamily 3, group C, member 1 (NR3C1), tumor necrosis factor (TNF), integrin alpha L (ITGAL), CXC chemokine receptor 2 (CXCR2), signal transducer and activator of transcription 1 (STAT1), integrin alpha 4 (ITGA4), leukemia inhibitory factor (LIF), RAS p21 protein activator 1 (RASA1), cadherin 5 (CDH5), ephrin B2 (EFNB2), regulator of G-protein signaling 16 (RGS16), chemokine (C—X—C motif) ligand 2 (CXCL2), integrin alpha 5 (ITGA5), chemokine (C—X—C motif) ligand 12 (CXCL12), tissue inhibitor of metalloprotease 1 (TIMP1), Fos-related antigen 2 (FOSL2), integrin beta 2 (ITGB2), and tissue inhibitor of metalloprotease 2 (TIMP2).

Another illustrative group of signature genes suitable for use in particular embodiments includes, but is not limited to: hairy/enhancer-of-split related with YRPW motif 1 (HEY1), GTP-binding protein GEM (GEM), dual specificity protein phosphatase 4 (DUSP4), amphiregulin (AREG), Nuclear receptor related 1 protein (NR4A2), renin (REN), cAMP-responsive element modulator (CREM), collagen, type I, alpha 1 (COL1A1), Fos-related antigen 2 (FOSL2), and UL16 binding protein 2 (ULBP2).

Another illustrative group of signature genes suitable for use in particular embodiments includes, but is not limited to: hyaluronan synthase 1 (HAS1), GTP-binding protein GEM (GEM), dual specificity protein phosphatase 4 (DUSP4), amphiregulin (AREG), Nuclear receptor related 1 protein (NR4A2), renin (REN), cAMP-responsive element modulator (CREM), collagen, type I, alpha 1 (COL1A1), Fos-related antigen 2 (FOSL2), and CXC chemokine receptor 4 (CXCR4).

A further illustrative group of genes signature genes includes, but is not limited to: CREM, GEM, NR4A2, NR4A3, IL1A, COX2, HEY1, CXCL2, CXCL3, and ULBP2.

Human HSPCs contacted with one or more agents and having enhanced therapeutic properties further comprise increased levels of intracellular cAMP signaling, e.g., CREB phosphorylation, or as determined by a biochemical assay; gene expression signatures indicating upregulation of genes implicated in the $PGE_2R_2/R_4$ cell signaling pathway, e.g., CREM, and genes that increase stem and progenitor cell homing and engraftment, e.g., CXCR4, as determined by gene expression assays, e.g., microarrays; no measurable decrease in stem and progenitor cell viability as determined by cell viability assays, e.g., 7-aminoactinomycinD (7-AAD) staining; and/or an increased capacity of stem cells to self-renew as determined by an in vitro colony forming units (CFU-C) assay, for example.

E. Agents

In various embodiments, compositions comprise blood cell products or hematopoietic stem or progenitor cells that have been contacted or treated with one or more agents that enhance one or more therapeutic properties of the cells. Without wishing to be bound to any particular theory, it is contemplated that the compositions and methods disclosed elsewhere herein for preparing hematopoietic cells for transplant further comprises for short-term treatment of the hematopoietic cells. Hematopoietic cells frozen, thawed, and reconstituted or resuspended in a medium comprising a polysaccharide, and optionally HSA, stabilize cell viability such that they can be treated with one or more agents to increase their therapeutic properties prior to transplant.

In one embodiment, a cryopreserved cell population is thawed and resuspended in a medium contemplated herein and then the hematopoietic cell population is modulated by contacting or culturing the cells with an agent. The cells may be thawed, resuspended, or modulated in the cell culture media of the invention containing a polysaccharide. As used herein, "agent" refers to a compound or molecule capable of increasing gene expression of one or more genes that indicated an increase in a therapeutic property of the hematopoietic cells treated with the agent. Particular agents include, for example, compounds capable of stimulating the prostaglandin pathway, e.g., a cAMP analogue or enhancer, a Gα-s activator, and a prostaglandin pathway agonist. Hematopoietic cells, in particular embodiments, may be treated, cultured, or contacted with one or more cytokines, growth factors, and/or glucocorticoids before and/or after, or in addition to contacting the cells with one or more agents that stimulate the prostaglandin pathway or in lieu of contacting the hematopoietic cells with one or more agents that stimulate the prostaglandin pathway.

Hematopoietic cells may be treated under conditions sufficient to increase the therapeutic properties of the cells. As used herein, the terms "conditions sufficient," or "under conditions sufficient," refer to the conditions for treating the hematopoietic cells with one or more agents to increase gene expression of one or more genes that indicates the increase in the therapeutic properties of the cells. Conditions include, but are not limited to the source of the cells, the agents used to treat the cells and concentrations of agent(s), the time the cells are exposed to the agent(s), and the temperature of treatment. Therapeutic properties increased by contacting with one or more of the agents contemplated herein include, but are not limited to: engraftment, reconstitution, homing, survival, and proliferation.

In particular embodiments, compositions comprise one or more agents, each at a final concentration of about 1 μM to about 100 μM. In certain embodiments, compositions comprise one or more agents, each at a final concentration of about $1 \times 10^{-14}$ M to about $1 \times 10^{-3}$ M, about $1 \times 10^{-13}$ M to about $1 \times 10^{-4}$ M, about $1 \times 10^{-12}$ M to about $1 \times 10^{-5}$ M, about $1 \times 10^{-11}$ M to about $1 \times 10^{-4}$ M, about $1 \times 10^{-11}$ M to about $1 \times 10^{-5}$ M, about $1 \times 10^{-10}$ M to about $1 \times 10^{-4}$ M, about $1 \times 10^{-10}$ M to about $1 \times 10^{-5}$ M, about $1 \times 10^{-9}$ M to about $1 \times 10^{-4}$ M, about $1 \times 10^{-9}$ M to about $1 \times 10^{-5}$ M, about $1 \times 10^{-8}$ M to about $1 \times 10^{-4}$ M, about $1 \times 10^{-7}$ M to about $1 \times 10^{-4}$ M, about $1 \times 10^{-6}$ M to about $1 \times 10^{-4}$ M, or any intervening ranges of final concentrations.

In another particular embodiment, compositions comprise blood cell products or hematopoietic cells treated with one or more agents, each at a final concentration of about $1 \times 10^{-14}$ M, about $1 \times 10^{-13}$ M, about $1 \times 10^{-12}$ M, about $1 \times 10^{-10}$ M, about $1 \times 10^{-9}$ M, about $1 \times 10^{-8}$ M, about $1 \times 10^{-7}$ M to about $1 \times 10^{-6}$ M, about $1 \times 10^{-5}$ M, about $1 \times 10^{-4}$ M, about $1 \times 10^{-3}$ M, or any intervening final concentration. In treatments comprising one or more agents, the agents can be at different concentrations from each other or at the same concentration.

In particular embodiments, compositions comprise hematopoietic cells that are intermittently, episodically, or sequentially contacted with one or more agents within the same vessel (e.g., contacting the population of cells with one drug for a period of time, exchanging the culture medium and/or washing the population of cells, then repeating the cycle with the same or a different combination of pharmaceutical agents for the same predetermined period of time or a different predetermined period of time).

1. Prostaglandin Pathway Agonists

As used herein, the term "prostaglandin pathway agonist" refers to an agent that stimulates prostaglandin cell signaling pathways, including an agent that stimulates the $PGE_2R_2$ and/or $PGE_2R_4$ cell signaling pathways, and increases CXCR4 gene expression in the cells. Illustrative examples of prostaglandin pathway agonists that are suitable for use in preparing cells of the invention, include, but are not limited to, $PGE_2$, dmPGE$_2$, 15(S)-15-methyl PGE$_2$, 20-ethyl PGE$_2$, 8-iso-16-cyclohexyl-tetranor PGE$_2$, and PGE$_2$ analogues. In certain embodiments, $PGE_2R_2$ and $PGE_2R_4$ agonists and analogues thereof are of particular interest, and in some embodiments, the agent preferentially binds and activates a $PGE_2$ $EP_2$ or $PGE_2$ $EP_4$ receptor.

As used herein, the terms "prostaglandin E$_2$" or "PGE$_2$" include, without limitation, any naturally-occurring or chemically synthesized PGE$_2$ molecule, as well as "analogues" thereof. As used herein, the term "analogue" or relates to a chemical molecule that is similar to another chemical substance, e.g., PGE$_2$, in structure and function, often differing structurally by a single element or group, but may differ by modification of more than one group (e.g., 2, 3, or 4 groups) if it retains the same function as the parental chemical. Such modifications are routine to persons skilled in the art, and include, for example, additional or substituted chemical moieties, such as esters or amides of an acid, protecting groups such as a benzyl group for an alcohol or thiol, and tert-butoxylcarbonyl groups for an amine. Also included are modifications to alkyl side chains, such as alkyl substitutions (e.g., methyl, dimethyl, ethyl, etc.), modifications to the level of saturation or unsaturation of side chains, and the addition of modified groups such as substituted phenyl and phenoxy. Analogues can also include conjugates, such as biotin or avidin moieties, enzymes such as horseradish peroxidase and the like, and including radio-labeled, bioluminescent, chemoluminescent, or fluorescent moieties. Also, moieties may be added to the agents described herein to alter their pharmacokinetic properties, such as to increase half-life in vivo or ex vivo, or to increase their cell penetration properties, among other desirable properties. Also included are prodrugs, which are known to enhance numerous desirable qualities of pharmaceuticals (e.g., solubility, bioavailability, manufacturing, etc.) (see, e.g., WO/2006/047476 for exemplary EP agonist prodrugs, which is incorporated by reference for its disclosure of such agonists).

Illustrative examples of PGE$_2$ "analogues" include, without limitation, 16,16-dimethyl PGE$_2$ ("dmPGE$_2$"), 16,16-dimethyl PGE$_2$ p-(p-acetamidobenzamido) phenyl ester, 11-deoxy-16,16-dimethyl PGE$_2$, 9-deoxy-9-methylene-16, 16-dimethyl PGE$_2$, 9-deoxy-9-methylene PGE$_2$, 9-keto Fluprostenol, 5-trans $PGE_2$, 17-phenyl-omega-trinor $PGE_2$, $PGE_2$ serinol amide, $PGE_2$ methyl ester, 16-phenyl tetranor $PGE_2$, 15(S)-15-methyl $PGE_2$, 15(R)-15-methyl $PGE_2$, 8-iso-15-keto $PGE_2$, 8-iso $PGE_2$ isopropyl ester, 8-iso-16-cyclohexyl-tetranor $PGE_2$, 20-hydroxy $PGE_2$, 20-ethyl $PGE_2$, 11-deoxy $PGE_1$, nocloprost, sulprostone, butaprost, 15-keto $PGE_2$, and 19 (R) hydroxy $PGE_2$. Also included are PG analogues or derivatives having a similar structure to $PGE_2$ that are substituted with halogen at the 9-position (see, e.g., WO 2001/12596, herein incorporated by reference in its entirety), as well as 2-decarboxy-2-phosphinico prostaglandin derivatives, such as those described in U.S. Publication No. 2006/0247214, herein incorporated by reference in its entirety).

Stimulation/activation of the $PGE_2R_2$ ($EP_2$) and $PGE_2R_4$ ($EP_4$) cell signaling pathways are contemplated to underlie the physiological responses in HSPCs that increase engraftment, maintain cell viability, and increase homing and proliferation of the cells. Accordingly, in one embodiment, a "non-$PGE_2$-based ligand" that binds to and stimulates $PGE_2R_2$ and $PGE_2R_4$ receptors (i.e., a $PGE_2R_2/PGE_2R_4$ agonist) is contemplated for use in the methods of the invention.

Illustrative examples of non-$PGE_2$-based $EP_2$ receptor agonists include CAY10399, ONO_8815Ly, ONO-AE1-259, CP-533,536 and carbazoles and fluorenes disclosed in WO 2007/071456.

Illustrative examples of non-$PGE_2$-based $EP_4$ agonists include ONO-4819, APS-999 Na, AH23848, ONO-AE1-329, and other non-$PGE_2$-based $EP_4$ agonists disclosed in WO/2000/038663; U.S. Pat. No. 6,747,037; and U.S. Pat. No. 6,610,719).

Agents selective for the $PGE_2$ $EP_4$ receptor preferentially bind to and activate $PGE_2$ $EP_4$ receptors. Such agents have a higher affinity for the $EP_4$ receptor than for any of the other three EP receptors namely $EP_1$, $EP_2$ and $EP_3$. Agents that selectively bind the PGE $EP_4$ receptor include, but are not limited to, agents selected from the group consisting of: 5-[(1E,3R)-4,4-difluoro-3-hydroxy-4-phenyl-1-buten-1-yl]-1-[6-(2H-tetrazol-5R-yl)hexyl]-2-pyrrolidinone; 2-[3-[(1R,2S,3R)-3-hydroxy-2-[(E,3S)-3-hydroxy-5-[2-(methoxymethyl)phenyl]pent-1-enyl]-5-oxocyclopentyl]sulfanylpropylsulfanyl]acetic acid; methyl 4-[2-[(1R,2R,3R)-3-hydroxy-2-[(E,3 S)-3-hydroxy-4-[3-(methoxymethyl)phenyl]but-1-enyl]-5-oxocyclopentyl]ethylsulfanyl]butanoate; 16-(3-Methoxymethyl)phenyl-rotetranor-5-thiaPGE; 5-{3-[(2S)-2-{(3R)-3-hydroxy-4-[3-(trifluoromethyl)phenyl]butyl}-5-oxopyrrolidin-1-yl]propyl]thiophene-2-carboxylate; [4'-[3-butyl-5-oxo-1-(2-trifluoromethyl-phenyl)-1,5-dihydro-[1,2,4]triazol-4-ylmethyl]-biphenyl-2-sulfonic acid (3-methyl-thiophene-2-carbonyl)-amide]; and ((Z)-7-{(1R,4S,5R)-5-[(E)-5-(3-chloro-benzo[b]thiophene-2-yl)-3-hydroxy-pent-1-enyl]-4-hydroxy-3,3-dimethyl-2-oxo-cyclopentyl}-hept-5-enoic acid), and pharmaceutically acceptable salts of any of these agents.

In particular embodiments, the prostaglandin pathway agonist is $PGE_2$, $dmPGE_2$, 15(S)-15-methyl $PGE_2$, 20-ethyl $PGE_2$, or 8-iso-16-cyclohexyl-tetranor $PGE_2$.

2. cAMP Enhancer

A "cyclic AMP (cAMP) enhancer," refers to a molecule that produces or causes a greater amount of cAMP in a cell, or a greater amount of cAMP activity in a cell, or any other relevant component of a cAMP related signal transduction pathway, or a measurable downstream physiological response or effect of a cAMP signaling pathway, as compared to no agent or a control molecule/composition.

Illustrative examples of cAMP enhancers include, but are not limited to phorbol ester, forskolin, sclareline, 8-bromo-cAMP, cholera toxin (CTx), aminophylline, 2,4 dinitrophenol (DNP), norepinephrine, epinephrine, isoproterenol, isobutylmethylxanthine (IBMX), caffeine, theophylline (dimethylxanthine), dopamine, rolipram, iloprost, prostaglandin E1, prostaglandin E2, pituitary adenylate cyclase activating polypeptide (PACAP), and vasoactive intestinal polypeptide (VIP), among others known in the art. Other examples of cAMP enhancers include cAMP and analogues of cAMP, such sp-5,6-DCl-BIMPS (BIMPS) and dibutyryl cAMP (dbcAMP), among others.

3. Gα-s Activators

A "Gα-s activator or activating agent" or "G-protein alpha-s activator or activating agent" includes any molecule capable of activating the alpha subunit of the stimulatory G-protein ("Gα-s") or variants of Gα-s.

Illustrative examples of Gα-s activators include $PGE_2$ and agonists and derivatives thereof, and cholera toxin.

4. Glucocorticoids

Illustrative examples of glucocorticoids and glucocorticoid receptor agonists suitable for use in the methods of the invention include, but are not limited to, medrysone, alclometasone, alclometasone dipropionate, amcinonide, beclometasone, beclomethasone dipropionate, betamethasone, betamethasone benzoate, betamethasone valerate, budesonide, ciclesonide, clobetasol, clobetasol butyrate, clobetasol propionate, clobetasone, clocortolone, cloprednol, cortisol, cortisone, cortivazol, deflazacort, desonide, desoximetasone, desoxycortone, desoxymethasone, dexamethasone, diflorasone, diflorasone diacetate, diflucortolone, diflucortolone valerate, difluorocortolone, difluprednate, fluclorolone, fluclorolone acetonide, fludroxycortide, flumetasone, flumethasone, flumethasone pivalate, flunisolide, flunisolide hemihydrate, fluocinolone, fluocinolone acetonide, fluocinonide, fluocortin, fluocoritin butyl, fluocortolone, fluorocortisone, fluorometholone, fluperolone, fluprednidene, fluprednidene acetate, fluprednisolone, fluticasone, fluticasone propionate, formocortal, halcinonide, halometasone, hydrocortisone, hydrocortisone acetate, hydrocortisone aceponate, hydrocortisone buteprate, hydrocortisone butyrate, loteprednol, meprednisone, 6a-methyl-prednisolone, methylprednisolone, methylprednisolone acetate, methylprednisolone aceponate, mometasone, mometasone furoate, mometasone furoate monohydrate, paramethasone, prednicarbate, prednisolone, prednisone, prednylidene, rimexolone, tixocortol, triamcinolone, triamcinolone acetonide and ulobetasol, as well as combinations thereof.

In particular embodiments, the glucocorticoid comprises medrysone, hydrocortisone, triamcinolone, alclometasone, or dexamethasone. In more particular embodiments, the glucocorticoid is medrysone.

F. Hematopoietic Cell Preparation Methods

Methods contemplated herein provide improved preparation of blood cell products and/or hematopoietic cells for transplants. In particular embodiments, a method comprises either or both of cryopreservation and thawing of blood cell products or hematopoietic cells and transfer of the thawed cells into a culture medium contemplated herein. Hematopoietic cells may be isolated, modulated, and/or expanded either prior to cryopreservation or following thawing of a previously cryopreserved or noncryopreserved (fresh) blood cell product. Without wishing to be bound by any particular theory, the culture media is contemplated to be useful in resuspension, processing, isolating, modulating, and/or expanding fresh or frozen blood cells products. In one embodiment, the culture media improve cell viability, decrease cell lysis, and increase the biological activity and therapeutic properties of fresh blood cell products. Accordingly, cryopreserved or thawed cells or fresh cells can further be isolated, modulated, or expanded in a culture medium contemplated herein.

In one embodiment, a method of stabilizing a hematopoietic cell population for transplantation is provided. In a particular embodiment, the method comprises thawing a cryopreserved blood cell product or population of hematopoietic cells and tranfser into a culture medium contemplated herein. The stabilized cell population has reduced cell lysis and increased CD34+ cell viability compared to a thawed control cell population that has been transferred to a control solution, e.g., 10% dextran, 5% HSA, and 0.9% NaCl, or defined culture medium alone.

In a particular embodiment, a method of reducing hematopoietic cell lysis in a population of cells for transplantation is provided. In a particular embodiment, the method comprises thawing a cryopreserved blood cell product or population of hematopoietic cells and transfer into a culture medium contemplated herein. In particular embodiments, the lysis is reduced about 10%, about 20%, about 30%, about 40%, about 50%, about two-fold, about three-fold, or about five-fold compared to a thawed control cell population that has been transferred to a control solution.

In one embodiment, a method of increasing hematopoietic cell viability in a population of cells for transplantation is provided. In a particular embodiment, the method comprises thawing a cryopreserved blood cell product or population of hematopoietic cells and transfer into a culture medium contemplated herein. In certain embodiments, the CD34+ cell viability is increased about 10%, about 20%, about 30%, about 40%, about 50%, about two-fold, about three-fold, or about five-fold compared to a thawed control cell population that has been transferred to a control solution.

In a certain embodiment, a method of increasing total nucleated cell (TNC) count in a population of cells for transplantation is provided. In a particular embodiment, the method comprises thawing a cryopreserved blood cell product or population of hematopoietic cells and transferring into a culture medium contemplated herein. In certain embodiments, the TNC is increased about 10%, about 20%, about 30%, about 40%, about 50%, about two-fold, about three-fold, or about five-fold compared to a thawed control cell population that has been transferred to a control solution.

1. Cryopreservation

In one embodiment, a blood cell product or population of hematopoietic cells can be divided and frozen in one or more bags (or units). In another embodiment, two or more cell populations can be pooled, divided into separate aliquots, and each aliquot frozen. As used herein, the terms "frozen/freezing" and "cryopreserved/cryopreserving" are used interchangeably. In particular embodiments, cryopreservation includes known methods that freeze cells in viable form. Cryopreservation causes cell injury by osmotic effects on the cell membrane, cell dehydration, solute concentration, and ice crystal formation. As ice forms outside the cell, available water is removed from solution and withdrawn from the cell, causing osmotic dehydration and raised solute concentration which may eventually destroy the cell. For a discussion, see Mazur, P., 1977, Cryobiology 14:251-272.

These injurious effects can be reduced by using a cryoprotective agent such as dimethyl sulfoxide (DMSO), glycerol, polyvinylpyrrolidine, polyethylene glycol, ethylene glycol, i-erythritol, D-ribitol, D-mannitol, D-sorbitol, i-inositol, D-lactose, choline chloride, amino acids, methanol, acetamide, glycerol monoacetate, and inorganic salts, (b) control of the freezing rate, and (c) storage at a temperature sufficiently low to minimize degradative reactions.

In a preferred embodiment, DMSO is used, a liquid which is nontoxic to cells in low concentration. Being a small molecule, DMSO freely permeates the cell and protects intracellular organelles by combining with water to modify its freezability and prevent damage from ice formation. Addition of plasma (e.g., to a concentration of 20-25%) or a plasma substitute (Plasmalyte) can augment the protective effect of DMSO. After addition of DMSO, cells should be kept at 0° C. until freezing, since DMSO concentrations of about 1% are toxic at temperatures above 4° C.

A controlled slow cooling rate can be used to reduce freezing-induced cellular damage. Different cryoprotective agents have different optimal cooling rates. The cooling procedure can be carried out by use of, e.g., a programmable freezing device or a methanol bath procedure.

After thorough freezing, the blood cell product or hematopoietic cells can be rapidly transferred to a long-term cryogenic storage vessel. In one embodiment, samples can be cryogenically stored in liquid nitrogen (−196° C.) or its vapor (−165° C.). Such storage is greatly facilitated by the availability of highly efficient liquid nitrogen refrigerators, which resemble large Thermos containers with an extremely low vacuum and internal super insulation, such that heat leakage and nitrogen losses are kept to an absolute minimum. Suitable racking systems are commercially available and can be used for cataloguing, storage, and retrieval of individual specimens.

2. Thawing

In various embodiments, compositions and methods contemplated herein offer numerous advantages in the thawing of previously frozen blood cell products and hematopoietic cells. Without wishing to be bound by any particular theory, it is contemplated that thawing frozen blood cell products and hematopoietic cells and transferring the thawed cells into the culture media contemplated herein increases total nuclear cell (TNC) count and hematopoietic cell viability and allows for subsequent processing, modulation, and/or expansion of the cells. It is further contemplated that thawing blood cell products and transferring the thawed cells into in the culture media stabilizes the membranes of apoptosing cells, thereby decreasing cell lysis, preventing cell debris aggregation, and preventing the release of intracellular components that can inhibit cellular processes; thus, the methods of thawing blood cell products and transferring the thawed cells into in the culture media contemplated herein provides populations of higher quality hematopoietic cells for transplant therapies.

In one embodiment, a cryopreserved population of cells comprising DMSO or other cryoprotective agents is thawed and diluted about two-fold, about three-fold, about four-fold, about five-fold, about six-fold, about seven-fold, about eight-fold, about nine-fold, about ten-fold or more in a culture medium contemplated herein and used in subsequent steps of preparing the cells for transplant. The diluted cell composition can then be washed and resuspended in a culture medium contemplated herein or used in subsequent steps of preparing the cells for transplant. In a particular embodiment, the thawed cells can then be further processed, modulated, or expanded. In a certain embodiment, the thawed cells can be directly infused into a human subject in need thereof.

In one embodiment, a method of preparing cryopreserved blood cell products for transplantation is provided. In particular embodiments, the method comprises thawing a cryopreserved blood cell product or population of hematopoietic cells, e.g., hematopoietic stem and progenitor cells. In certain embodiments, the thawed cells are transferred into a culture medium contemplated herein, and optionally prepared for infusion into a subject, either immediately or following one or more steps of processing, modulation, or expansion.

In a particular embodiment, the blood cell product or hematopoietic cells are thawed at a temperature of about 20° C. to about 37° C., about 25° C. to about 37° C., about 30° C. to about 37°, or about 35° C. to about 37° C. In a certain embodiment, the blood cell product or hematopoietic cells are thawed at a temperature of about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., or about 37° C.

3. Processing Hematopoietic Cells

In various embodiments, methods contemplated herein provide improved preparation of blood cell products and/or hematopoietic cells for transplants comprising a step of processing the blood cell products or cells. As used herein, the term "processing" refers to a step of washing, purifying, or otherwise manipulating a blood cell product.

Blood cell products can be washed any number of times between other isolation, freezing, thawing, resuspending, modulating, and expanding steps. For example, blood cell products may be washed 1, 2, 3, 4, 5 or more times between each step of manipulating or handling the blood cell product. Illustrative wash solutions for washing blood cell products include physiological saline, Ringer's solution, low molecular weight dextran, and HSA in 0.9% NaCl. In particular embodiments, a blood cell product may also be washed one or more times with a chemically defined medium.

In other embodiments, a blood cell product may be processed so as to remove portions of the product to improve downstream manipulation. For example, whole cord blood, placental blood, or mobilized peripheral blood may be processed to remove red blood cells and plasma. In particular embodiments, red blood cells are removed to minimize blood type incompatibilities reactions to between donor and recipient.

In one embodiment, the blood cell product or hematopoietic cells are processed such that the cell population is about 75%, about 80%, about 85%, about 90%, about 95%, or about 100% hematopoietic cells or CD34$^+$ cells. In some embodiments, the population of cells is less than about 0.1%, 0.5%, 1%, 2%, 5%, 10%, 15%, 20%, 25%, or 30% hematopoietic cells or CD34$^+$ cells.

In particular embodiments, the processed population of cells comprises populations of hematopoietic stem or progenitor cells or CD34$^+$ cells and is substantially free of mesenchymal stem cells and/or endothelial progenitor cells. In certain embodiments, the population of cells comprises hematopoietic stem or progenitor cells or CD34$^+$ cells less than about 30%, 25%, 20%, 15%, 10% or 5% mesenchymal stem cells and less than about 30%, 25%, 20%, 15%, 10% or 5% endothelial progenitor cells.

Populations of cells may alternatively be depleted of mesenchymal stem cells and/or endothelial progenitor cells using methods known in the art, for example, using immunomagnetic selection techniques, fluorescence activated cell sorting, or a combination therein, CD34$^+$ cells may be purified from any number of cell sources disclosed herein and suitable for use in the present invention.

4. Modulating Hematopoietic Cells

In various embodiments, use of the culture media contemplated herein offers particular advantages over existing methods of manipulating blood cell products. In addition to increasing cell viability, the culture media allow manipulated cells to retain or increase biological activity and therapeutic properties. Products such as whole cord blood that is cultured in the culture media contemplated herein comprise changes in gene expression, including increases in gene expression that are representative of a therapeutic gene expression signature, that are normally low or absent in the same products treated in the absence of the culture media contemplated herein. For example, whole cord blood treated with one or more agents (e.g., a prostaglandin pathway agonist) as described elsewhere herein shows increased gene expression of signature genes that indicate that the cells are imbued with therapeutic properties compared to whole cord blood manipulated in control solutions, as described elsewhere herein.

In one embodiment, compositions comprise blood cell products or hematopoietic cells treated ex vivo with one or more agents capable of increasing CXCR4 gene expression conditions sufficient to increase CXCR4 gene expression at least about 2, 3, 4, 5, 10, 15, 20, 30, 40, 50, 60, 70, or 80 fold in the contacted cells compared to non-contacted cells. In particular embodiments, the hematopoietic cells are contacted with one or more agents after thawing a frozen blood cell product or hematopoietic cells from a subject. In another embodiment, hematopoietic cells are cryopreserved; thawed, resuspended, and/or purified in a culture medium contemplated herein, and modulated and/or expanded by contacting the cells with one or more agents in a culture medium contemplated herein.

In particular embodiments, HSPCs are treated with one or more agents in an amount effective and for a time sufficient (i.e., under conditions sufficient) to increase CXCR4 gene expression at least about 2, 3, 4, 5, 10, 15, 20, 30, 40, 50, 60, 70, or 80 fold in the contacted cells compared to non-contacted cells.

In certain embodiments, sufficient temperature conditions include incubation of the blood cell product or hematopoietic cells with the one or more agents at a physiologically relevant temperature, such as a temperature range of about 22° C. to about 39° C. (about room temperature to about body temperature), including but not limited to temperatures of about 22° C., 23° C., 24° C., 25° C., 26° C., 27° C., 28° C., 29° C., 30° C., 31° C., 32° C., 33° C., 34° C., 35° C., 36° C., 37° C., 38° C., and 39° C. In a particular embodiment, the sufficient temperature condition is between about 35° C. and 39° C. In one embodiment, the sufficient temperature condition is about 37° C.

In a particular embodiment, a sufficient concentration of an agent is a final concentration of about 10 nM to about 100 µM, about 100 nM, about 500 nM, about 1 µM, about 10 µM, about 20 µM, about 30 µM, about 40 µM, about 50 µM, about 60 µM, about 70 µM, about 80 µM, about 90 µM, about 100 µM, about 110 µM, or about 120 µM, or any other intervening concentration of the agent (e.g., 0.1 µM, 1 µM, 5 µM, 10 µM, 20 µM, 50 µM, 100 µM). In a particular embodiment, the sufficient concentration of each agent is a final concentration of about 10 µM to about 25 µM. In one embodiment, the sufficient concentration of an agent is a final concentration of about 10 µM.

In further embodiments, the sufficient time period for treating a blood cell product or a population of hematopoietic cells with one or more agents is an incubation period of about 60 minutes to about 24 hours, about 60 minutes to about twelve hours, about 60 minutes to about 6 hours, about 2 hours to about 6 hours, about 2 hours to about 4 hours, and including, but not limited to, treatment for a duration of about 60 minutes, about 70 minutes, about 80 minutes, about 90 minutes, about 100 minutes, about 110 minutes, about 2 hours, about 2.5 hours, about 3 hours, about 3.5 hours or about 4 hours or any other intervening duration. In a particular embodiment, the sufficient incubation period is about 2 hours to about 4 hours. In one embodiment, the sufficient incubation period for treating the HSPCs is about four hours.

In various embodiments, conditions sufficient to increase CXCR4 gene expression at least about 2, 3, 4, 5, 10, 15, 20, 30, 40, 50, 60, 70, or 80 fold in the contacted cells compared to non-contacted cells comprises treating HSPCs ex vivo at a temperature range of about 22° C. to about 39° C.; at a final concentration of about 10 µM to about 25 µM of a prostaglandin pathway agonist, and about 10 µM to about 25 µM of a glucocorticoid; and incubation with the agents for about 1 hour to about 4 hours, for about 2 hours to about 3 hours, for about 2 hours to about 4 hours, or for about 3 hours to about 4 hours.

In particular embodiments, conditions sufficient to increase CXCR4 gene expression at least about 2, 3, 4, 5, 10, 15, 20, 30, 40, 50, 60, 70, or 80 fold in the contacted cells compared to non-contacted cells comprises treating HSPCs ex vivo at a temperature range of about 22° C. to about 39° C.; at a final concentration of about 10 µM to about 25 µM of $PGE_2$ or $dmPGE_2$, and about 10 µM to about 25 µM of a glucocorticoid; and incubation with the agents for about 1 hour to about 4 hours, for about 2 hours to about 3 hours, for about 2 hours to about 4 hours, or for about 3 hours to about 4 hours. In various embodiments, conditions sufficient to increase CXCR4 gene expression at least about 2, 3, 4, 5, 10, 15, 20, 30, 40, 50, 60, 70, or 80 fold in the contacted cells compared to non-contacted cells comprises treating HSPCs ex vivo at a temperature range of about 37° C., at a final concentration of about 10 µM 16,16-$dmPGE_2$, for a duration of about 2 hours.

In particular embodiments, methods contemplated herein comprise modulating a blood cell product or hematopoietic cells to increase gene expression of two or more genes in a gene expression signature or panel.

One illustrative example of a suitable gene expression panel includes HEY1, COX2, ULBP2, HAST, GEM1, REN, COL1A1, ANGPT1, CXCL6, PROM1, BMP4, ANGPT2, IKBKB, PECAM1, TIE1, AREG, CASP3, JAG1, ARNT, CREM, CTGF, CD40L, BAX, HGF, SOD2, PDGFB, THBS1, DUSP4, CYR61, CXCL1, TEK, CFLAR, IGF2, CXCR4, MMP2, FGF2, PTGS2, RAC2, PDGFR, NR4A2, NR4A3, TERT, TGFB1, MMP9, CD40, CD44, HMGB1, NOS3, KDR, ITGB1, CTNNB1, CSF3, IL8, PLAUR, BCL2, BMP2, CSF1, AKT1, VEGFA, ICAM1, CXCL3, CASP8, CD34, IL1A, CD47, CCL7, HIF1A, EDN1, S1PR1, CCR1, SMAD4, FLT1, CD151, PGF, NFKB1, SMAD2, CXCR7, TGFB3, CXCL5, CCND1, HBEGF, NR3C1, TNF, ITGAL, CXCR2, STAT1, ITGA4, L1F, RASA1, CDH5, EFNB2, RGS16, CXCL2, ITGA5, CXCL12, TIMP1, FOSL2, ITGB2, and TIMP2.

In another embodiment, a blood cell product or population of hematopoietic cells is modulated to increase gene expression of a plurality of the signature genes selected from the group consisting of: CREM, GEM, NR4A2, NR4A3, IL1A, COX2, HEY1, CXCL2, CXCL3, and ULBP2. The modulated cells may have increased expression of 2, 3, 4, 5, 6, 7, 8, 9, or 10 signature genes compared to expression levels in control or untreated cells.

In particular embodiments, a blood cell product or population of hematopoietic cells is modulated to increase gene expression of at least two genes, at least five genes, at least 10 genes, at least 25 genes, at least 50 genes, or at least 100 or more genes, or any intervening number of signature genes. In preferred embodiments, a blood cell product or population of hematopoietic cells is modulated to increase gene expression of about 2 to about 25 genes, about 2 to about 10 genes, or about 5 to about 10 genes, or any intervening range of genes thereof.

In certain embodiments, a blood cell product or population of hematopoietic cells is deemed to be sufficiently modulated when the expression of at least 2, 3, 4, or 5 signature genes is increased about 80-fold, about 70-fold, about 60-fold, about 50-fold, about 40-fold, about 30-fold, about 20-fold, about 10-fold, about 5-fold, about 3-fold, or about 2-fold compared to expression of the genes in a control population of cells. In additional embodiments, a blood cell product or population of hematopoietic cells is sufficiently modulated when the expression of at least 10, 20, 30, 40, 50, 60, 70, 80, or 90 signature genes, or any intervening number of genes thereof, is increased about 80-fold, about 70-fold, about 60-fold, about 50-fold, about 40-fold, about 30-fold, about 20-fold, about 10-fold, about 5-fold, about 3-fold, or about 2-fold compared to expression of the genes in a control population cells.

In various embodiments, the modulated hematopoietic cells comprise increased therapeutic properties including, increased engraftment, increased engraftment potential, increased hematopoietic reconstitution, increased hematopoietic reconstitution potential, increased homing, increased homing potential, increased proliferation and increased proliferation potential. In particular embodiments, these increased therapeutic properties are increased compared to a blood cell product or hematopoietic cells contacted with a control or vehicle composition (10% dextran, 5% HSA, 0.9% NaCl or defined culture medium alone).

5. Expanding Hematopoietic Cells

In one embodiment, compositions comprise blood cell products or a population of cells comprising hematopoietic cells treated ex vivo with one or more agents to expand hematopoietic stem and progenitor cells. In a particular embodiment, cells are contacted with one or more agents that promote growth and expansion of hematopoietic stem and progenitor cells during ex vivo treatments, such as prior to, during, and/or after transplant procedures (see, e.g., WO 2008/073748, herein incorporated by reference in its entirety). Likewise, also according to the methods provided herein, ex vivo expansion of HSPCs in the presence of a prostaglandin pathway agonist or an analog thereof prior to hematopoietic cell transplantation can improve engraftment and reconstitution of hematopoiesis and immune function after transplant (see, e.g., Lord et al., Cell Cycle 6:3054-7, 2007, herein incorporated by reference in its entirety).

Therefore, in particular embodiments, methods of preparing cells for a transplant contemplated herein comprise stimulating hematopoietic stem cell (HSC) growth or expansion, as well as the growth or expansion of other stem-like cells (e.g., multi-potent cells, pluripotent cells, etc.) comprising transferring the blood cell product or heamtopoietic cell population into a culture medium contemplated herein, contacting the cells with one or more prostaglandin pathway agonists, and incubating the cells for a time sufficient to stimulate growth or expansion of the HSPCs, and thereby stimulating HPSC growth or expansion.

G. Methods of Treatment or Therapeutic Methods

The compositions and methods of preparing cells contemplated herein are useful in a variety of clinical settings, including cell transplantation, treatment of hematological disorders, diseases, and conditions, treatment of ischemia, and gene therapy. In particular embodiments, the compositions comprising blood cell products or hematopoietic cells are useful in increasing engraftment, reconstitution, homing, and proliferation of cell grafts in a subject in need thereof.

"Subjects in need thereof" include, but are not limited to a subject in need of hematopoietic engraftment, reconstitution, homing, proliferation, or gene therapy. Included are subjects that have or that have been diagnosed with various types of leukemias, anemias, lymphomas, myelomas, immune deficiency disorders, and solid tumors as discussed elsewhere herein. A "subject" also includes a human who is a candidate for stem cell transplant or bone marrow transplantation, such as during the course of treatment for a malignant disease or a component of gene therapy. In particular embodiments, a subject receives genetically modified HSPCs as a cell-based gene therapy. Subjects may also include individuals or animals that donate stem cells or bone marrow for allogeneic transplantation. In certain embodiments, a subject may have undergone myeloablative irradiation therapy or chemotherapy, or may have experienced an acute radiation or chemical insult resulting in myeloablation. In certain embodiments, a subject may have undergone irradiation therapy or chemotherapy, such as during various cancer treatments. Typical subjects include animals that exhibit aberrant amounts (lower or higher amounts than a "normal" or "healthy" subject) of one or more physiological activities that can be modulated by an agent or a stem cell or marrow transplant.

Subjects in need of hematopoietic engraftment or reconstitution include subjects undergoing chemotherapy or radiation therapy for cancer, as well as subjects suffering from (e.g., afflicted with) non malignant blood disorders, particularly immunodeficiencies (e.g. SCID, Fanconi's anemia, severe aplastic anemia, or congenital hemoglobinopathies, or metabolic storage diseases, such as Hurler's disease, Hunter's disease, mannosidosis, among others) or cancer, particularly hematological malignancies, such as acute leukemia, chronic leukemia (myeloid or lymphoid), lymphoma (Hodgkin's or non-Hodgkin's), multiple myeloma, myelodysplastic syndrome, or non-hematological cancers such as solid tumors (including breast cancer, ovarian cancer, brain cancer, prostate cancer, lung cancer, colon cancer, skin cancer, liver cancer, or pancreatic cancer).

Subjects also include subjects suffering from aplastic anemia, an immune disorder (severe combined immune deficiency syndrome or lupus), myelodysplasia, thalassemaia, sickle-cell disease or Wiskott-Aldrich syndrome. In some embodiments, the subject suffers from a disorder that is the result of an undesired side effect or complication of another primary treatment, such as radiation therapy, chemotherapy, or treatment with a bone marrow suppressive drug, such as zidovadine, chloramphenical or gangciclovir. Such disorders include neutropenias, anemias, thrombocytopenia, and immune dysfunction.

Other subjects may have disorders caused by an infection (e.g., viral infection, bacterial infection or fungal infection) which causes damage to stem or progenitor cells of the bone marrow.

In addition, subject suffering from the following conditions can also benefit from treatment using cell-based compositions of the invention: lymphocytopenia, lymphorrhea, lymphostasis, erythrocytopenia, errthrodegenerative disorders, erythroblastopenia, leukoerythroblastosis; erythroclasis, thalassemia, myelofibrosis, thrombocytopenia, disseminated intravascular coagulation (DIC), immune (autoimmune) thrombocytopenic purpura (ITP), HIV inducted ITP, myelodysplasia; thrombocytotic disease, thrombocytosis, congenital neutropenias (such as Kostmann's syndrome and Schwachman-Diamond syndrome), neoplastic associated—neutropenias, childhood and adult cyclic neutropaenia; post-infective neutropaenia; myelodysplastic syndrome; neutropaenia associated with chemotherapy and radiotherapy; chronic granulomatous disease; mucopolysaccharidoses; Diamond Blackfan; sickle cell disease; β-thalassemia major; Gaucher's disease; Krabbe's disease; metachromatic leukodystrophy; Tay-Sachs; Nieman Pick; glycoproteinoses (e.g., fucosidosis, a-mannosidosis); and MPS-III (Sanfillipo).

In a particular embodiment, the subject is a bone marrow donor who has donated bone marrow, is a bone marrow donor who has yet to donate bone marrow, is a bone marrow donor transplant recipient, has hematopoietic progenitor cells under environmental stress, has anemia, has a reduced level of immune cell function compared to a normal subject, or has an immune system deficiency.

In a certain embodiment, the subject has myeloma, non-Hodgkin's lymphoma, Hodgkin's lymphoma, chronic myeloid leukemia, chronic myelogenous leukemia, chronic granulocytic leukemia, acute lymphoblastic leukemia, acute nonlymphoblastic leukemia, or pre-leukemia.

Subject also include those in need of treatment for ischemic tissue or one or more symptoms associated with tissue ischemia, including, but not limited to, impaired, or loss of, organ function (including without limitation impairments or loss of brain, kidney, or heart function), cramping, claudication, numbness, tingling, weakness, pain, reduced wound healing, inflammation, skin discoloration, and gangrene. As used herein, the terms "ischemia," "ischemic condition," or "ischemic event" mean any decrease or stoppage in the blood supply to any cell, tissue, organ, or body part caused by any constriction, damage, or obstruction of the vasculature. Ischemia sometimes results from vasoconstriction or thrombosis or embolism. Ischemia can lead to direct ischemic injury, tissue damage due to cell death caused by reduced supply of oxygen (hypoxia, anoxia), glucose, and nutrients. "Hypoxia" or a "hypoxic condition" intends a condition under which a cell, organ or tissue receives an inadequate supply of oxygen. "Anoxia" refers to a virtually complete absence of oxygen in the organ or tissue, which, if prolonged, may result in death of the cell, organ or tissue.

In particular embodiments, the subject is in need of gene therapy, such as, for example, a hemoglobinopathy. As used herein, the term "hemoglobinopathy" or "hemoglobinopathic condition" includes any disorder involving the presence of an abnormal hemoglobin molecule in the blood. Examples of hemoglobinopathies included, but are not limited to, hemoglobin C disease, hemoglobin sickle cell disease (SCD), sickle cell anemia, and thalassemias. Also included are hemoglobinopathies in which a combination of abnormal hemoglobins is present in the blood (e.g., sickle cell/Hb-C disease).

The term "sickle cell anemia" or "sickle cell disease" is defined herein to include any symptomatic anemic condition which results from sickling of red blood cells. Manifestations of sickle cell disease include: anemia; pain; and/or organ dysfunction, such as renal failure, retinopathy, acute-chest syndrome, ischemia, priapism and stroke. As used herein the term "sickle cell disease" refers to a variety of clinical problems attendant upon sickle cell anemia, especially in those subjects who are homozygotes for the sickle cell substitution in HbS. As used herein, the term "thalassemia" encompasses hereditary anemias that occur due to mutations affecting the synthesis of hemoglobin. Thus, the term includes any symptomatic anemia resulting from thalassemic conditions such as severe or β-thalassemia, thalassemia major, thalassemia intermedia, α-thalassemias such as hemoglobin H disease.

In one embodiment, a method of cell-based therapy, comprises administering to a subject in need thereof, a blood cell product or a population of hematopoietic cells thawed and transferring into a culture medium contemplated herein, optionally wherein the cells have been processed, modulated, or expanded. In various embodiments, the cells are hematopoietic cells, such as, for example, hematopoietic stem or progenitor cells (e.g., isolated from umbilical cord blood or mobilized peripheral blood), optionally treated with one or more agents to increase one or more therapeutic properties of the cells. In a certain embodiment, the cells are treated with a prostaglandin pathway agonist, e.g., 16,16-dmPGE$_2$, optionally at a concentration of 10 μM, for a time of about 2 hours, at 37° C.

Administration of an "amount" of cells prepared herein to a subject refers to administration of "an amount effective," to achieve the desired therapeutic or prophylactic result, including without limitation, treatment of the subject. A "therapeutically effective amount" of cells for purposes herein is thus determined by such considerations as are known in the art, and may vary according to factors such as the disease state, age, sex, and weight of the individual, and the ability of the cells to elicit a desired response in the individual. The term "therapeutically effective amount" includes an amount that is effective to "treat" a subject (e.g., a patient). A therapeutically effective amount is also one in which any toxic or detrimental effects of the cells are outweighed by the therapeutically beneficial effects.

A "prophylactically effective amount" refers to an amount of cells having therapeutic potential that is effective to achieve the desired prophylactic result. Typically but not necessarily, since a prophylactic dose is used in subjects prior to or at an earlier stage of disease, the prophylactically effective amount is less than the therapeutically effective amount.

Suitable methods for administering populations of cells used in the methods described herein include parenteral administration, including, but not limited to methods of intravascular administration, such as intravenous and intraarterial administration. Additional illustrative methods for administering cells of the invention include intramuscular, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

In various embodiments, the blood cell product or hematopoietic cells administered to a subject are a heterogeneous population of cells including, whole bone marrow, umbilical cord blood, mobilized peripheral blood, hematopoietic stem cells, hematopoietic progenitor cells, and the progeny of hematopoietic stem and progenitor cells, including granulocytes (e.g., promyelocytes, myelocytes, metamyelocytes, neutrophils, eosinophils, basophils), erythrocytes (e.g., reticulocytes, erythrocytes), thrombocytes (e.g., megakaryoblasts, platelet producing megakaryocytes, platelets), and monocytes (e.g., monocytes, macrophages).

Particular embodiments of the present invention now will be described more fully by the following examples. This invention may, however, be embodied in many different forms and should not be construed as limited to the embodiments set forth herein; rather, these embodiments are provided so that this disclosure will be thorough and complete, and will fully convey the scope of the invention to those skilled in the art.

EXAMPLES

Example 1

STEMSPAN-ACF+Dextran-40 Minimizes Loss of Viable CD34$^+$ Cells and Improves TNC Recovery During Short-Term Incubation of Whole Cord Blood CD34 Enumeration of Cord Blood During Short-Term Incubation Cord blood units were obtained from the Carolinas Cord Blood Bank (CBB). Samples from these cord blood units were thawed in StemSpan-ACF (Stem Cell Technologies, Vancouver, BC, Canada) or StemSpan-ACF with 8% Dextran-40 (Sigma-Aldrich, St Louis, Mo.) at 37° C. Each sample was centrifuged at 400×g for 10 minutes and resuspended in the same medium in which each sample was initially thawed. Both samples were incubated for 2 hours at 37° C. 100 uL samples were drawn from both conditions throughout the processing and incubation. BD Stem Cell Enumeration Kit (BD Biosciences, San Jose, Calif.) standard no-lyse, no-wash protocol for cord blood units was used to stain the cells for CD34-PE, CD45-FITC, and 7AAD. The samples were analyzed on a BD FACSCanto II (BD Biosciences, San Jose, Calif.) and gated using ISHAGE gating strategy. The percentage of granulocytes was estimated using a gate set around the granulocyte population with characteristic high side scatter and low CD45 surface expression.

Results

More viable CD34$^+$ cells were enumerated in the samples incubated in STEMSPAN-ACF with 8% Dextran-40 compared to STEMSPAN-ACF alone at one hour and after two hours of incubation (post-incubation) at 37° C. (FIG. 1a). Post-incubation, the number of viable CD34$^+$ cells was 36% less in samples incubated in STEMSPAN-ACF compared to samples incubated in STEMSPAN with Dextran-40.

Figure 1B:
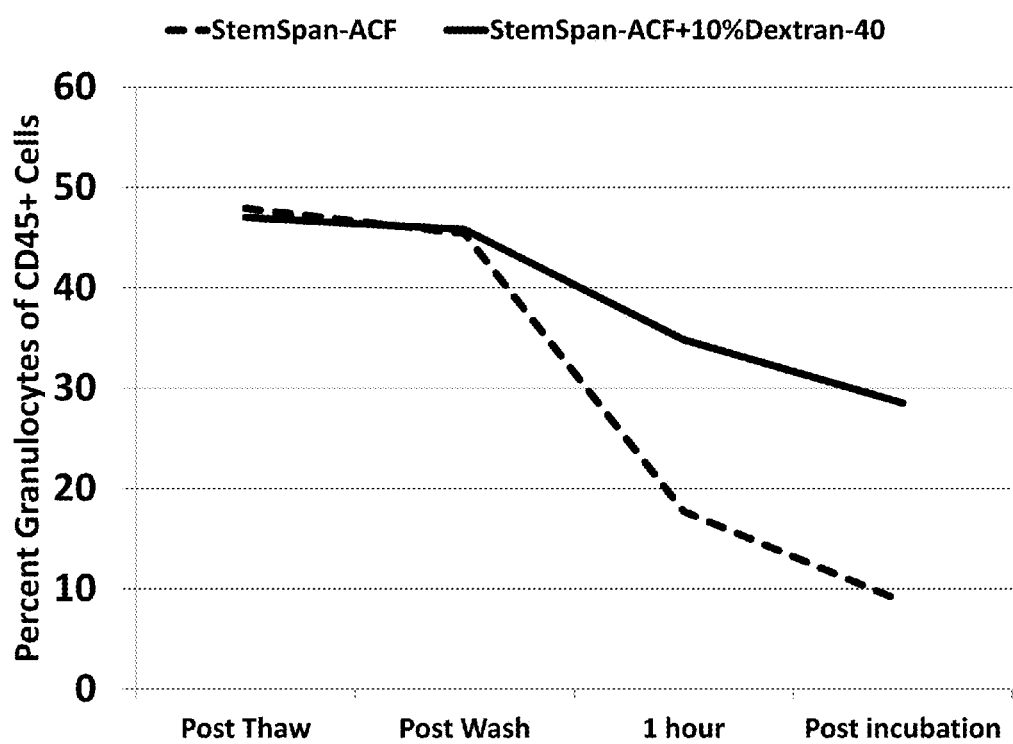
FIG. 1B shows the percentage of intact granulocytes in the $CD45^+$ cell fraction in the sample incubated in STEMSPAN-ACF with 8% Dextran compared to STEMSPAN alone at post-thaw, post-wash, after one hour of incubation at 37° C. and after two hours of incubation at 37° C. (post-incubation).

The percentage of intact granulocytes in the CD45$^+$ cell fraction increased about 20% in the sample incubated in STEMSPAN-ACF with 8% Dextran versus STEMSPAN alone at one hour and after two hours of incubation (post-incubation) at 37° C. (FIG. 1b). This result indicated that a smaller fraction of granulocytes lysed during the incubation.

Example 2

STEMSPAN-ACF+Dextran-40 Increases TNC in Whole Cord Blood Treated with DMPGE$_2$ Ex Vivo Modulation of a Whole Cord Blood Unit with dmPGE2

Cord blood units were obtained from Carolinas CBB and stored in liquid nitrogen (LN$_2$) vapor phase. The cord blood units were RBC-reduced and plasma-reduced prior to cryopreservation and stored in a volume of 25 mL. The cord blood units were thawed in a 37° C. water bath and the volume was brought to 45 mL in STEMSPAN-ACF, STEMSPAN ACF+2.1% HSA, STEMSPAN+4.2% HSA, IMDM +4.2% HSA, or STEMSPAN-ACF with 8% Dextran-40. A Sepax 2 cell processing system (Biosafe, Geneva, Switzerland) was used to wash the cord blood units with the same media in which the cord blood units were initially thawed.

The total volume of the washed cord blood units was 95 mL. dmPGE2 was added to the cord blood units to a final concentration of 10 µM. The cord blood units were placed into a Plasmatherm device (Barkey, Leopoldshoehe, Germany) for 2 hours at 37° C. with constant paddle-mixing. The total nucleated cell (TNC) count was determined using a Sysmex KX-21N (Sysmex America, Inc, Lincolnshire, Ill.) after thawing, washing, and incubation steps.

Results

Figure 2:
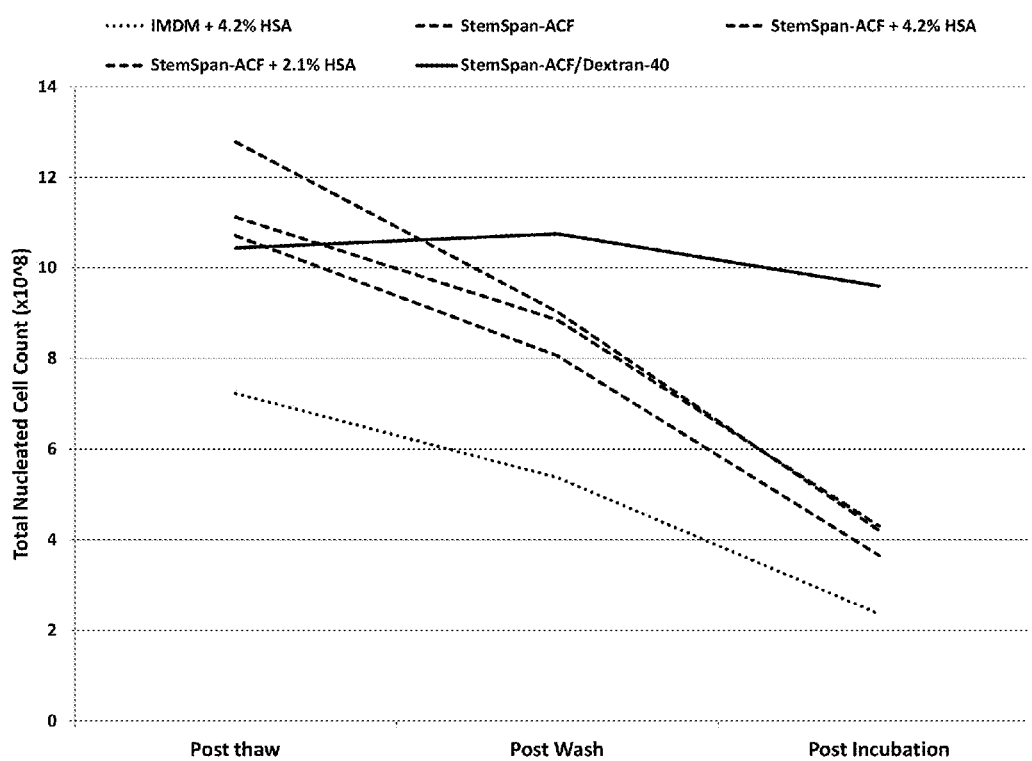
FIG. 2 shows the TNC count for the cord blood units treated with 10 µM dmPGE2 and processed in STEMSPAN-ACF, STEMSPAN-ACF+2.1% HSA, STEMSPAN+4.2% HSA, IMDM+4.2% HSA, or STEMSPAN-ACF with 8% Dextran-40 at post-thaw, post-wash, and after two hours of incubation at 37° C.

The TNC count for the cord blood units processed in STEMSPAN-ACF or IMDM resulted in an average TNC loss of 65.4% from thaw to post-incubation as compared to an 8.0% loss of TNC in STEMSPAN-ACF with 8% Dextran-40 (FIG. 2). One observable difference between these units was the cellular debris clumping in media without Dextran-40. Most of the loss of TNC occurred during the incubation but some loss also occurred during the washing of the cord blood unit.

Example 3

Whole Cord Blood Treated with dmPGE$_2$ Maintains Biological Activity in STEMSPAN-ACF+Dextran-40

Addition of Dextran-40 to STEMSPAN-ACF Does Not Inhibit Biological Activities

Cord blood mononuclear cells (All Cells, Emeryville, Calif.) were thawed in a 37° C. water bath and immediately diluted with 10 mL of pre-warmed IMDM with 10% fetal calf serum and 5 µL of DNase (Life Technologies, Grand Island, N.Y.). The cells were split three ways and centrifuged at 300×g for 10 minutes. The cells were resuspended in STEMSPAN-ACF (Media 1), STEMSPAN-ACF with 5% Dextran-40 (Media 2) or STEMSPAN-ACF with 10% Dextran-40 (Media 3). A subset, 1×10$^6$ cells, from Media 1 were kept at 4° C. and immediately stained with Lineage MixFITC, CXCR4-PE, CD34-APC, and CD45-V450 antibodies from BD Biosciences. All 3 media conditions were split into a vehicle-treated cohort and a 10 mM dmPGE2-treated cohort and incubated at 37° C. for 2 hours. The cells were washed with the same media and incubated at 37° C. for an additional 1 hour. Each cohort was stained with the same antibodies as indicated above. Levels of CXCR4 surface protein within the Lin-CD45$^{low}$CD34$^+$ 7AAD-cells were analyzed.

Results

Figure 3:
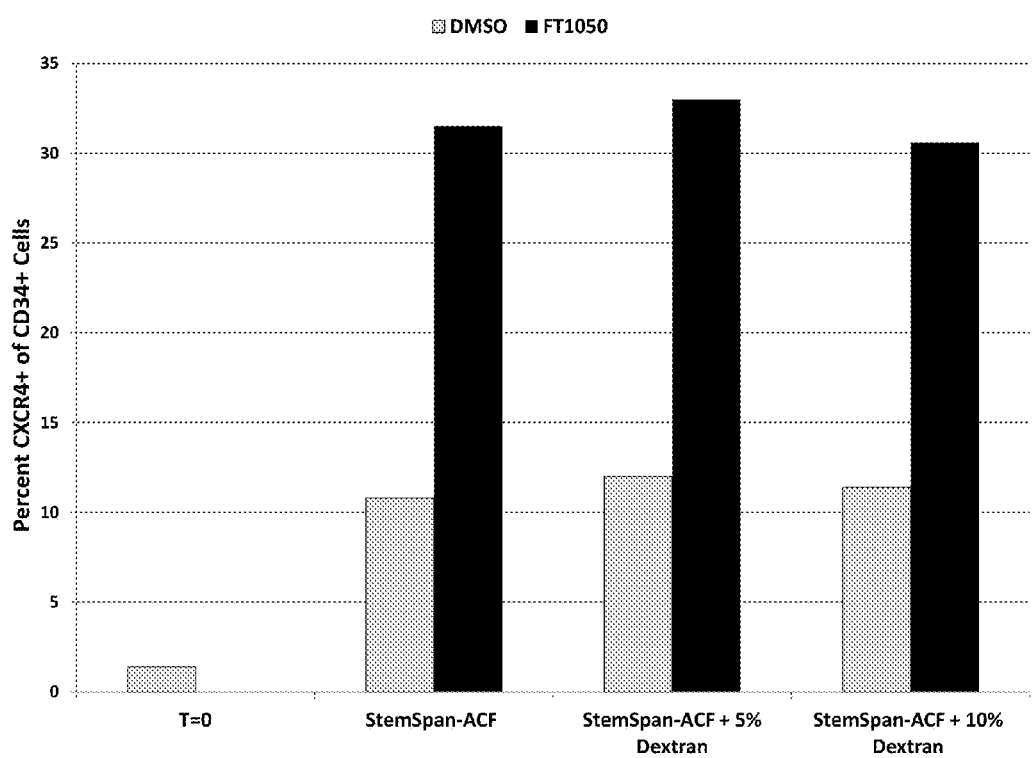
FIG. 3 shows the percent of $CD34^+$ cells that show increased CXCR4 expression after incubation with 10 µM dmPGE2 for two hours at 37° C. Samples were treated with STEMSPAN-ACF, STEMSPAN-ACF+5% Dextran-40, or STEMSPAN+10% Dextran-40.

After incubation with 10 µM dmPGE2 for two hours at 37° C., increased CXCR4 gene expression was observed, and after an additional one hour incubation without dmPGE2, CXCR4 surface protein was increased. The addition of 5% or 10% Dextran-40 to STEMSPAN-ACF did not decrease the response of CD34$^+$ cells to dmPGE2 as evidenced by the increased level of CXCR4 surface protein expression (FIG. 3).

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A composition comprising:
   a) about 5% to about 10% dextran;
   b) a chemically defined cell culture medium; and
   c) one or more cloned growth factors or one or more cytokines;
   wherein said composition does not contain fetal calf serum or an animal-derived lipid.

2. The composition of claim 1, wherein the dextran is selected from the group consisting of: dextran-1, dextran-10, dextran-20, dextran-30, and dextran-40.

3. The composition of claim 2, wherein the dextran is dextran-40.

4. The composition of 1, wherein the composition comprises about 10% dextran.

5. The composition of claim 1, wherein the chemically defined cell culture medium is selected from the group consisting of: Iscove's modified Dulbecco's medium (IMDM), Roswell Park Memorial Institute medium (RPMI) 1640 medium, McCoy's 5A medium, minimum essential medium alpha medium (alpha-MEM), basal medium Eagle (BME), Fischer's medium, medium199, F-12K nutrient mixture medium (Kaighn's modification, F-12K), and X-vivo 20.

6. The composition of claim 1, wherein the one or more cloned growth factors or cytokines are selected from the group consisting of: flt3-ligand (FLT3); thrombopoietin (TPO), stem cell factor (SCF), epidermal growth factor (EGF), transforming growth factor-beta (TGF-β), basic fibroblast growth factor (bFGF), interleukin-3 (IL3), interleukin-6 (IL6), and interleukin-9 (IL9).

7. The composition of claim 1, further comprising an agent selected from the group consisting of a cAMP analogue or enhancer, a Gα-s activator, and a prostaglandin pathway agonist.

8. The composition of claim 7, wherein the prostaglandin pathway agonist selectively binds the prostaglandin E2 (PGE2) EP2 or the PGE2 EP4 receptor.

9. The composition of claim 7, wherein the prostaglandin pathway agonist comprises PGE2, or a PGE2 analogue or derivative.

10. The composition of claim 7, wherein the prostaglandin pathway agonist is selected from the group consisting of: PGE2, 16, 16-dmPGE2, 15(S)-15-methyl PGE2, 20-ethyl PGE2, and 8-iso-16-cyclohexyl-tetranor PGE2.

11. The composition of claim 7, wherein the prostaglandin pathway agonist comprises 16, 16-dmPGE2.

12. The composition of claim 1, further comprising a population of cells.

13. The composition of claim 12, wherein the population of cells is selected from the group consisting of: bone marrow cells (BMCs), umbilical cord blood cells (UCBCs), placental blood cells, mobilized peripheral blood cells (mPBCs), hematopoietic stem cells (HSCs), hematopoietic progenitor cells (HPCs), and CD34$^+$ cells.

14. The composition of claim 13, wherein the HSCs comprise a purified population of CD34$^+$ cells.

15. The composition of claim 1, wherein the chemically defined cell culture medium comprises Iscove's modified Dulbecco's medium (IMDM), bovine serum albumin, insulin, transferrin, and vitamins.

16. A method comprising: thawing a whole cord blood sample, transferring the sample into a culture medium comprising the composition of claim 1, and modulating the sample in the culture medium by contacting the sample with an agent that modulates a prostaglandin pathway for a duration of about 1 to about 24 hours, at a temperature of about 25° C. to about 37° C. comprising a total nucleated cell (TNC) of at least 70%, wherein the sample is not subject to enrichment.

17. A composition comprising:
  a) about 5% to about 10% polysaccharide;
  b) a chemically defined cell culture medium; and
  c) one or more cloned growth factors;
  wherein said composition does not contain fetal calf serum;
wherein the composition comprises: Calcium Chloride Anhydrous; Cupric Sulfate; Ferric Nitrate; Ferric Sulfate; Potassium Chloride; Magnesium Chloride; Magnesium Sulfate; Sodium Chloride; Sodium Bicarbonate; Sodium Phosphate Monobasic; Sodium Phosphate dibasic; Zinc Sulfate; D-Glucose (Dextrose); Phenol Red; 4-(2-hydroxyethyl)-1-piperazineethanesulfonic acid (HEPES); Sodium Hypoxanthine; Linoleic acid; DL-68-Thioctic Acid; Sodium Putrescine; Putrescine 8 Sodium Selenite; Sodium Pyruvate; Alanine; Arginine; Asparagine; Aspartic acid; Cysteine; Cysteine; Glutamic acid; Glutamine; Glycine; Histidine; Isoleucine; Leucine; Lysine; Methionine; Phenylalanine; Proline; Serine; Threonine; Tryptophan; Tyrosine; Valine; Biotin; D-Calcium panthenate; Choline chloride; Folic acid; i-Inositol; Niacinamide; Pyridoxine; Riboflavine; Thiamine; Thymidine; and Vitamin B12.

18. The composition of claim 17, wherein the composition comprises: Calcium Chloride Anhydrous; Cupric Sulfate (CuSO4 5H2O); 0.0751 mg/L Ferric Nitrate (Fe(NO3) 9H2O); 0.0209 mg/L Ferric Sulfate (FeSO47H2O); 306.969 mg/L Potassium Chloride (KCl); 14.418 mg/L Magnesium Chloride (MgCl2); 63.237 mg/L Magnesium Sulfate (MgSO4); 5021.73 mg/L Sodium Chloride (NaCl); 1100 mg/L Sodium Bicarbonate (NaHCO4); 93.964 mg/L Sodium Phosphate Monobasic (NaH2PO4H2O); 35.753 mg/L Sodium Phosphate dibasic (Na2HPO4 7H2O); 0.217 mg/L Zinc Sulfate (ZnSO4 7H2); 3836.3 mg/L D-Glucose (Dextrose); 8.127 mg/L Phenol Red; 3099.505 mg/L HEPES; 1.203 mg/L Na Hypoxanthine; 0.0211 mg/L Linoleic acid; 0.0528 mg/L DL-68-Thioctic Acid; 0.0407 mg/L Sodium Putrescine 2HCl; 2.5×10-6 mg/L Putrescine 8 Sodium Selenite; 40.1885 mg/L Sodium Pyruvate; 3.24 mg/L Alanine; 116.255 mg/L Arginine HCl; 4.19 mg/L Asparagine; 3.347 mg/L Aspartic acid; 9.445 mg/L Cysteine H2O; 15.752 mg/L Cysteine 2HCl; 3.7 mg/L Glutamic acid; 293.55 mg/L Glutamine; 24.439 mg/L Glycine; 36.847 mg/L Histidine HCl H2O; 79.921 mg/L Isoleucine; 82.227 mg/L Leucine; 118.937 mg/L Lysine HCl; 23.679 mg/L Methionine; 50.861 mg/L Phenylalanine; 12.564 mg/L Proline; 34.214 mg/L Serine; 74.408 mg/L Threonine; 12.54 mg/L Tryptophan; 64.086 mg/L Tyrosine 2Na+2 H2O; 73.606 mg/L Valine; 0.00176 mg/L Biotin; 3.127 mg/L D-Calcium panthenate; 6.52 mg/L Choline chloride; 3.334 mg/L Folic acid; 9.904 mg/L i-Inositol; 3.079 mg/L Niacinamide; 3.022 mg/L Pyridoxine HCl; 0.31 mg/L Riboflavine; 3.092 mg/L Thiamine HCl; 0.183 mg/L Thymidine; and 0.512 mg/L Vitamin B12.

19. A method of preparing cryopreserved blood cell products for transplantation comprising:
  a) thawing a cryopreserved blood cell product; and
  b) transferring the thawed blood cell product to a composition comprising about 5% to about 10% dextran a chemically defined cell culture medium, and one or more cloned growth factors or cytokines; wherein said composition does not contain fetal calf serum or an animal-derived lipid.

20. The method of claim 19, wherein the dextran is selected from the group consisting of: dextran-1, dextran-10, dextran-20, dextran-30, and dextran-40.

21. The method of claim 20, wherein the composition comprises about 1% to about 10% HSA.

22. The method of claim 19, wherein the dextran is dextran-40.

23. The method of claim 19, wherein the composition comprises about 10% dextran.

24. The method of claim 19, wherein the chemically defined cell culture medium is selected from the group consisting of: Iscove's modified Dulbecco's medium (IMDM), Dulbecco's modified Eagle medium (DMEM), Roswell Park Memorial Institute medium (RPMI) 1640 medium, McCoy's 5A medium, minimum essential medium alpha medium (alpha-MEM), basal medium Eagle (BME), Fischer's medium, medium199, F-12K nutrient mixture medium (Kaighn's modification, F-12K), and X-vivo 20.

25. The method of claim 19, wherein the one or more cloned growth factors or cytokines are selected from the group consisting of: flt3-ligand (FLT3); thrombopoietin (TPO), stem cell factor (SCF), epidermal growth factor (EGF), transforming growth factor (TGF-β), basic fibroblast growth factor (bFGF), interleukin-3 (IL3), interleukin-6 (IL6), and interleukin-9 (IL9).

26. The method of claim 19, wherein the composition comprises an agent selected from the group consisting of a cAMP analogue or enhancer, a Gα-s activator, and a prostaglandin pathway agonist.

27. The method of claim 26, wherein the prostaglandin pathway agonist selectively binds the PGE2 EP2 or PGE2 EP4 receptor.

28. The method of claim 27, wherein the prostaglandin pathway agonist comprises PGE2, or a PGE2 analogue or a derivative.

29. The method of claim 27, wherein the prostaglandin pathway agonist is selected from the group consisting of: PGE2, 16,16-dmPGE2, 15(S)-15-methyl PGE2, 20-ethyl PGE2 and 8-iso-16-cyclohexyl-tetranor PGE2.

30. The method of claim 27, wherein the prostaglandin pathway agonist comprises 16,16-dmPGE2.

31. The method of claim 19, wherein the blood cell product is thawed at a temperature of about 20° C. to about 37° C.

32. The method of claim 31, wherein the blood cell product is thawed at a temperature of about 37° C.

33. The method of claim 19, wherein the blood cell product is selected from the group consisting of: bone marrow cells (BMCs), umbilical blood cells (UCBCs), placental blood cells, mobilized peripheral blood cells (mPBCs), hematopoietic stem cells (HSCs), hematopoietic progenitor cells (HPCs), and CD34$^+$ cells.

34. The method of claim 19, wherein the blood cell product comprises bone marrow, umbilical cord blood, placental blood, or mobilized peripheral blood.

35. The method of claim 19, wherein the blood cell product comprises purified population of CD34$^+$ cells.

36. The method of claim 19, wherein the cell lysis of the blood cell products is decreased about 10% to about 50% compared to the cell lysis of a control blood cell product.

37. The method of claim 19, wherein the CD34$^+$ cell viability of the blood cell product is increased about 10% to about 50% compared to the CD34$^+$ cell viability of a control hematopoietic cell population.

38. The method of claim 19, wherein the TNC count of the blood cell product is increased about 10% to about 50% compared to the TNC count of a thawed control blood cell product that has been transferred to a control solution.

39. The method of claim 19, wherein the blood cell product is modulated ex vivo.

40. The method of claim 39, wherein the modulation comprises contacting the blood cell product with an agent selected from the group consisting of: a cAMP analogue or enhancer, a Gα-s activator, and a prostaglandin pathway agonist.

41. The method of claim 40, wherein the prostaglandin pathway agonist selectively binds the PGE2 EP2 or PGE2 EP4 receptor.

42. The method of claim 40, wherein the prostaglandin pathway agonist comprises PGE2, or a PGE2 analogue or derivative.

43. The method of claim 40, wherein the prostaglandin pathway agonist is selected from the group consisting of: PGE2, 16,16-dmPGE2, 15(S)-15-methyl PGE2, 20-ethyl PGE2, and 8-iso-16-cyclohexyl-tetranor PGE2.

44. The method of claim 40, wherein the prostaglandin pathway agonist comprises 16,16-dmPGE2.

45. The method of claim 40, wherein the blood cell product is contacted with the agent for a time of about one hour to about four hours.

46. The method of claim 40, wherein the blood cell product is contacted with the agent at a temperature of about 25° C. to about 37° C.

47. The method of claim 46, wherein the blood cell product is contacted with the agent at a temperature of about 37° C.

48. The method of claim 39, wherein engraftment of the blood cell product is increased in vivo, compared to a non-modulated blood cell product.

49. The method of claim 39, wherein reconstitution of the blood cell product is increased in vivo, compared to a non-modulated blood cell product.

50. The method of claim 39, wherein the homing of the blood cell product is increased in vivo, compared to a non-modulated blood cell product.

51. The method of claim 39, wherein proliferation of the blood cell product is increased in vivo, compared to a non-modulated blood cell product.

52. The method of claim 19, wherein the blood cell product is administered to a subject.

53. The method of claim 52, wherein the blood cell product is allogeneic to the subject.

54. The method of claim 52, wherein the blood cell product is autologous to the subject.

55. The method of claim 52, wherein the subject has a disease, disorder, or condition selected from the group consisting of: ischemia, a non malignant blood disorder, an immunodeficiency, severe combined immunodeficiency (SCID), lymphocytopenia, thrombocytopenia, neutropenia, anemia, Fanconi's anemia, severe aplastic anemia, a congenital hemoglobinopathy, sickle cell disease, β-thalassemaia, sickle-cell disease, Wiskott-Aldrich syndrome, a metabolic storage disease, Hurler's disease, Hunter's disease, mannosidosis, a cancer, a hematological malignancy, acute leukemia, chronic myeloid leukemia, chronic lymphoid leukemia, Hodgkin's lymphoma, non-Hodgkin's lymphoma, multiple myeloma, myelodysplastic syndrome, a non-hematological cancer, breast cancer, ovarian cancer, brain cancer, prostate cancer, lung cancer, colon cancer, skin cancer, liver cancer, and pancreatic cancer.

* * * * *